(12) United States Patent
De Vleeschouwer et al.

(10) Patent No.: US 11,007,154 B2
(45) Date of Patent: May 18, 2021

(54) TREATMENT OF CENTRAL NERVOUS TUMOURS

(71) Applicants: KATHOLIEKE UNIVERSITEIT LEUVEN, Leuven (BE); UNIVERSITÉ LIBRE DE BRUXELLES, Brussels (BE)

(72) Inventors: Steven De Vleeschouwer, Heverlee (BE); Matthias Van Woensel, Westerlo (BE); Karim Amighi, Brussels (BE); Nathalie Wauthoz, Brussels (BE); Rémi Rosiere, Brussels (BE)

(73) Assignees: KATHOLIEKE UNIVERSITEIT LEUVEN, Leuven (BE); UNIVERSITÉ LIBRE DE BRUXELLES, Brussels (BE)

( * ) Notice: Subject to any disclaimer, the term of this patent is extended or adjusted under 35 U.S.C. 154(b) by 0 days.

(21) Appl. No.: 15/778,359

(22) PCT Filed: Nov. 23, 2016

(86) PCT No.: PCT/EP2016/078547
§ 371 (c)(1),
(2) Date: May 23, 2018

(87) PCT Pub. No.: WO2017/089392
PCT Pub. Date: Jun. 1, 2017

(65) Prior Publication Data
US 2018/0344658 A1    Dec. 6, 2018

(30) Foreign Application Priority Data
Nov. 23, 2015    (GB) .................................... 1520600

(51) Int. Cl.
| | |
|---|---|
| *C07H 21/04* | (2006.01) |
| *A61K 9/51* | (2006.01) |
| *A61K 9/00* | (2006.01) |
| *A61P 35/00* | (2006.01) |
| *A61K 31/7105* | (2006.01) |
| *A61K 47/69* | (2017.01) |
| *A61K 47/36* | (2006.01) |

(52) U.S. Cl.
CPC .......... *A61K 9/5161* (2013.01); *A61K 9/0043* (2013.01); *A61K 31/7105* (2013.01); *A61P 35/00* (2018.01); *A61K 9/5192* (2013.01); *A61K 47/36* (2013.01); *A61K 47/6939* (2017.08)

(58) Field of Classification Search
None
See application file for complete search history.

(56) References Cited

U.S. PATENT DOCUMENTS

| | | | |
|---|---|---|---|
| 7,964,575 B2 * | 6/2011 | Camby | ................ C12N 15/113 514/44 R |
| 2010/0120891 A1 | 5/2010 | Camby et al. | |
| 2011/0033547 A1 | 2/2011 | Kjems et al. | |
| 2013/0337067 A1 | 12/2013 | Prakash et al. | |

OTHER PUBLICATIONS

Techaarpornkul, Sunee, et al. "Chitosan-mediated siRNA delivery in vitro: effect of polymer molecular weight, concentration and salt forms." AAPS Pharmscitech 11.1 (2010): 64-72.*
Sarvaiya, Jayrajsinh, and Y. K. Agrawal. "Chitosan as a suitable nanocarrier material for anti-Alzheimer drug delivery." International journal of biological macromolecules 72 (2015): 454-465.*
Verschuere, Tina, et al. "Glioma-derived galectin-1 regulates innate and adaptive antitumor immunity." International journal of cancer 134.4 (2014): 873-884.*
Sharma, Ketan, et al. "Nebulised siRNA encapsulated crosslinked chitosan nanoparticles for pulmonary delivery." International journal of pharmaceutics 455.1-2 (2013): 241-247.*
European Office Action from EP Application No. 16805742.0, dated Mar. 13, 2019.
Astorgues-Xerri et al., "OTX008, a Selective Small-Molecule Inhibitor of Galectin-1, Downregulates Cancer Cell Proliferation, Invasion and Tumor Angiogenesis," European Journal of Cancer, vol. 50, 2014, pp. 2463-2477.
Camby et al., "Galectin-1 Modulates Human Glioblastoma Cell Migration into the Brain Through Modifications to the Actin Cytoskeleton and Levels of Expression of Small GTPases," Journal of Neuropathology and Experimental Neurology, vol. 61, No. 7, Jul. 2002, pp. 585-596.
Croci et al., "Glycosylation-Dependent Lectin-Receptor Interactions Preserve Angiogenesis in Anti-VEGF Refractory Tumors," Cell, vol. 156, Feb. 13, 2014, pp. 744-758.
Danhier et al., "Combined anti-Galectin-1 and anti-EGFR siRNA-loaded Chitosan-Lipid Nanocapsules Decrease Temozolomide Resistance in Glioblastoma: In Vivo Evaluation," International Journal of Pharmaceutics, vol. 481, 2015, pp. 154-161.
Davis et al., "Absorption Enhancers for Nasal Drug Delivery," Clin Pharmacokinet, vol. 42, No. 13, 2003, pp. 1107-1128.
Garín et al., "Galectin-1: a Key Effector of Regulation Mediated by CD4+CD25+T Cells," Blood, vol. 109, No. 5, Mar. 2007, pp. 2058-2066.
Grauer et al., "Immunotherapy of Diffuse Gliomas: Biological Background, Current Status and Future Developments," Brain Pathology, vol. 19, 2009, pp. 674-693.

(Continued)

*Primary Examiner* — Kimberly Chong
(74) *Attorney, Agent, or Firm* — Workman Nydegger

(57) ABSTRACT

The present invention generally relates to a new formulation containing nanoparticles encapsulating siRNA for the use of RNAi technology for gene silencing of galectin-1 involved in tumour progression. More in particular the present invention relates to the use of RNAi molecules for treating central nervous cancer, more in particular for treating glioblastoma multiforme (GBM).

Figure 3B:
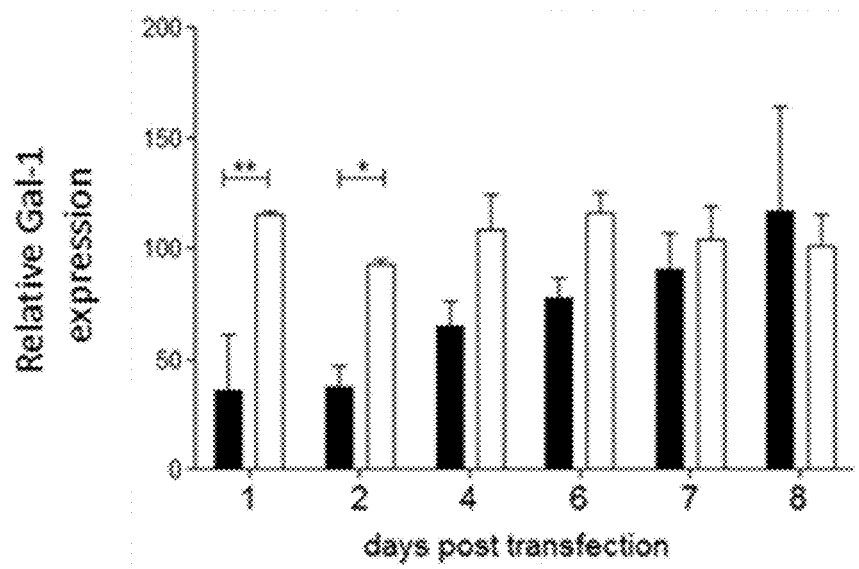
Figure 3C:
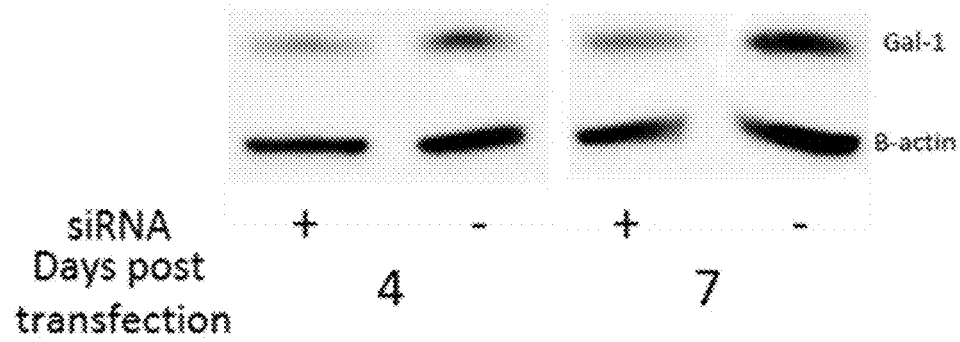
Figure 3D:
Figure 3E:
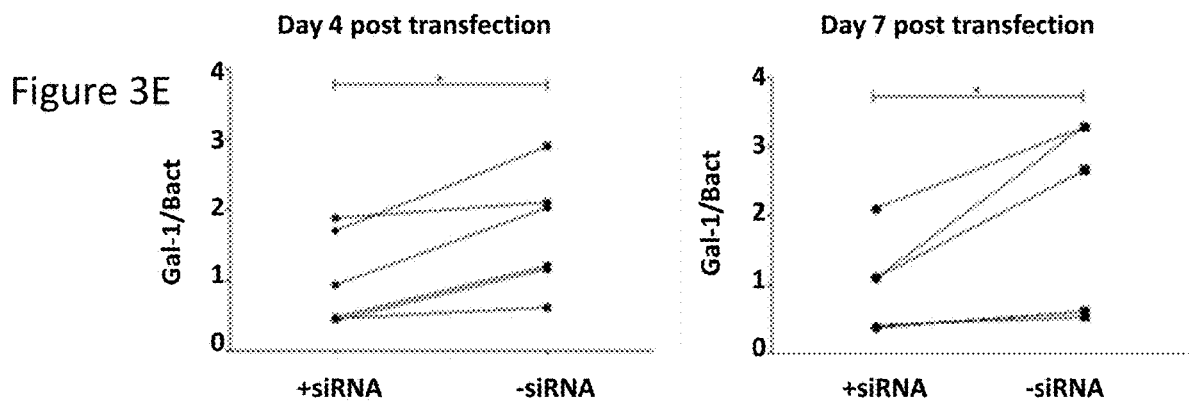
Figure 3F:
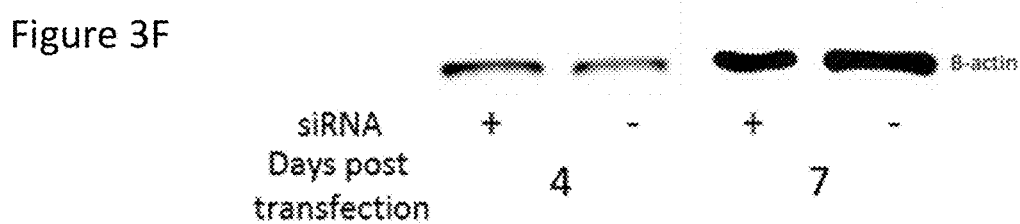

15 Claims, 8 Drawing Sheets
Specification includes a Sequence Listing.

(56) References Cited

OTHER PUBLICATIONS

Katas et al., "Development and Characterisation of Chitosan Nanoparticles for siRNA Delivery," Journal of Controlled Release, vol. 115, 2006, pp. 216-225.
Le Mercier et al., "Evidence of Galectin-1 Involvement in Glioma Chemoresistance," Toxicology and Applied Pharmacology, vol. 229, 2008, pp. 172-183.
Le Mercier et al., "Knocking Down Galectin 1 in Human Hs683 Gliboblastoma Cells Impairs Both Angiogenesis and Endoplasmic Reticulum Stress Responses," Neuropathol Exp Neural, vol. 67, No. 5, May 2008, pp. 456-469.
Le Mercier et al., "Galectins and Gliomas," Brain Pathology, vol. 20, 2010, pp. 17-27.
Lochhead et al., "Intranasal Delivery of Biologics to the Central Nervous System," Advanced Drug Delivery Reviews, vol. 64, 2012, pp. 614-628.
Louis et al., "The 2007 WHO Classification of Tumors of the Central Nervous System," Acta Neuropathol, vol. 114, 2007, pp. 97-109.
Maes et al., "Depletion of Regulatory T Cells in a Mouse Experimental Glioma Model Through Anti-CD25 Treatment Results in the Infiltration of Non-Immunosuppressive Myeloid Cells in the Brain," Hindawi Publishing Corporation Clinical and Developmental Immunology, vol. 2013, Article ID 952469, Apr. 3, 2013, 6 Pages.
Malhotra et al., "Intranasal Delivery of Chitosan-siRNA Nanoparticle Formulation to the Brain," Methods in Molecular Biology, Feb. 2014, 29 Pages.
Nel et al., "Understanding Biophysicochemical Interactions at the Nano-Bio Interface," Nature Materials, vol. 8, Jul. 2009, pp. 543-557.
Pardridge, "Blood-Brain Barrier Delivery," Drug Discovery Today, vol. 12, No. 1/2, Jan. 2007, pp. 54-61.
Rubinstein et al., "Targeted Inhibition of Galectin-1 Gene Expression in Tumor Cells Results in Heightened T Cell-Mediated Rejection: A Potential Mechanism of Tumor-Immune Privilege," Cancer Cell, vol. 5, Mar. 2004, pp. 241-251.
Schutze, "siRNA Technology," Molecular and Cellular Endocrinology, vol. 213, 2004, pp. 115-119.
Soane et al., "Clearance Characteristics of Chitosan Based Formulations in the Sheep Nasal Cavity," International Journal of Pharmaceutics, vol. 217, 2001, pp. 183-191.
Stupp et al., "Effects of Radiotherapy with Concomitant and Adjuvant Temozolomide Versus Radiotherapy Alone on Survival in Glioblastoma in a Radomised Phase III Study: 5-Year Analysis of the EORTC-NCIC Trial," Lancet Oncology, vol. 10, May 2009, pp. 459-466.
Thakker et al., "Neurochemical and Behaviroal Consequences of Widespread Gene Knockdown in the Adult Mouse Brain by Using Nonviral RNA Interference," Proceedings of the National Academy of Sciences of the United States of America, vol. 101, No. 49, pp. 17270-17275.
Toussaint III et al., "Galectin-1, a Gene Preferentially Expressed at the Tumor Margin, Promotes Glioblastoma Cell Invasion," Molecular Cancer, vol. 11, No. 32, 2012, 12 Pages.

Van Woensel et al., "Formulations for Intranasal Delivery of Pharmacological Agents to Combat Brain Disease: A New Opportunity to Tackle GBM?," Cancers, vol. 5, 2013, pp. 1020-1048.
Van Woensel et al., "Development of siRNA-Loaded Chitosan Nanoparticles Targeting Galectin-1 for the Treatment of Glioblastoma Multiforme via Intranasal Administration," Journal of Controlled Release, vol. 227, 2016, pp. 71-81.
Verschuere et al., "Glioma-Derived Galectin-1 Regulates Innate and Adaptive Antitumor Immunity," International Journal of Cancer, vol. 134, 2014, pp. 873-884.
Vllasaliu et al., "Tight Junction Modulation by Chitosan Nanoparticles: Comparison With Chitosan Solution," International Journal of Pharmaceutics, vol. 400, 2010, pp. 183-193.
Weathers et al., "Current Challenges in Designing GBM Trials for Immunotherapy," Journal of Neuro-Oncology, vol. 123, pp. 331-337.
Great Britain Search Report from GB Application No. GB 1520600. 6, dated Aug. 30, 2016.
International Search Report from PCT Application No. PCT/EP2016/078547, dated Mar. 28, 2017.
De Vleeschouwer et al., "Postoperative Adjuvant Dendritic Cell-Based Immunotherapy in Patients with Relapsed Glioblastoma Multiforme," Clinical Cancer Research 2008, vol. 14, No. 10, May 15, 2008, pp. 3098-3104.
De Vleeschouwer et al., "Stratification According to HGG-IMMUNO RPA Model Predicts Outcome in a Large Group of Patients with Relapsed Malignant Glioma Treated by Adjuvant Postoperative Dendritic Cell Vaccination," Cancer Immunol Immunother, vol. 61, May 8, 2012, pp. 2105-2112.
Camby et al., "Galectin-1: A Small Protein With Major Functions," Glycobiology, vol. 16, No. 11, Jul. 11, 2006, pp. 137R-157R.
Debinski et al., "Convection-Enhanced Delivery for the Treatment of Brain Tumors," Expert Review Neurotherapeutics, vol. 9, No. 10, Oct. 2009, pp. 1519-1527.
Illum, "Transport of Drugs from the Nasal Cavity to the Central Nervous System," European Journal of Pharmaceutical Sciences, vol. 11, Mar. 10, 2000, 18 Pages.
Mistry et al., "Nanoparticles for Direct Nose-to-Brain Delivery of Drugs," International Journal of Pharmaceutics, vol. 379, Jun. 16, 2009, pp. 146-157.
Groothuis, "The Blood-Brain and Blood-Tumor Barriers: A Review of Strategies for Increasing Drug Delivery," Neuro-Oncology, Jan. 2000, pp. 45-59.
Kim et al., "Intranasal Delivery of HMGB1 siRNA Confers Target Gene Knockdown and Robust Neuroprotection in the Postischemic Brain," Molecular Therapy, vol. 20, No. 4, Apr. 2012, pp. 829-839.
Hashizume et al., "New Therapeutic Approach for Brain Tumors: Intranasal Delivery of Teleomerase Inhibitor GRN 163," Neuro-Oncology, vol. 10, Feb. 20, 2008, pp. 112-120.
Bernkop-Schnürch et al., "Chitosan-Based Drug Delivery Systems," European Journal of Pharmaceutics and Biopharmaceutics, vol. 81, Apr. 16, 2012, pp. 463-469.
Malhotra et al., "Intranasal, siRNA Delivery to the Brain by TAT/MGF Tagged PEGylated Chitosan Nanoparticles," Hindawi Publishing Corporation Journal of Pharmaceutics, vol. 2013, Article ID 812387, Aug. 9, 2013, 10 Pages.
Bonferoni et al., "Chitosan and its Salts for Mucosal and Transmucosal Delivery," Expert Opinion Drug Delivery, vol. 6, No. 9, 2009, pp. 923-939.

* cited by examiner

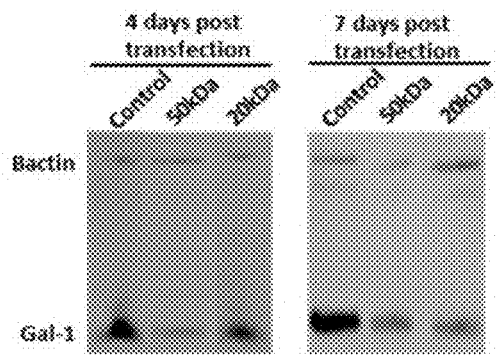 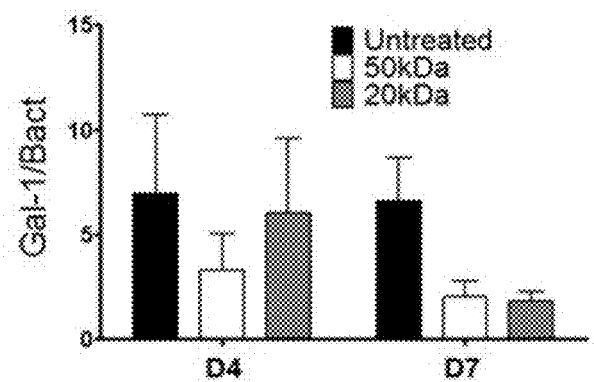
Figure 1A					Figure 1B
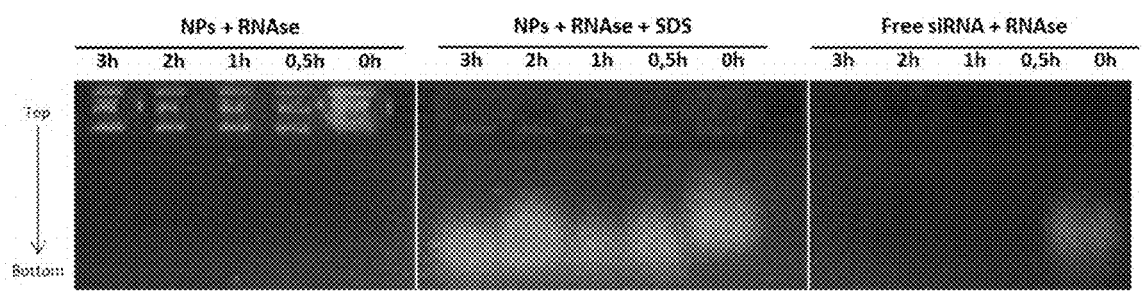
Figure 2
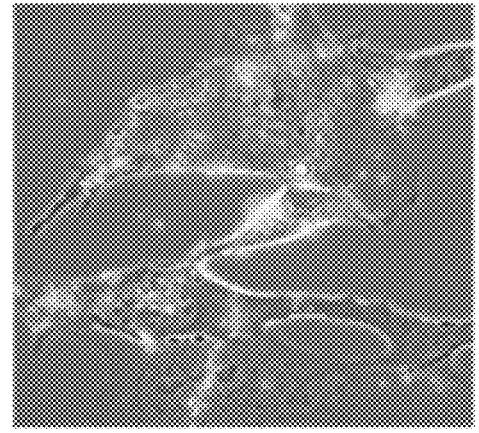
Figure 3A

SEQUENCE LISTING

```
<160> NUMBER OF SEQ ID NOS: 10

<210> SEQ ID NO 1
<211> LENGTH: 19
<212> TYPE: RNA
<213> ORGANISM: Artificial Sequence
<220> FEATURE:
<223> OTHER INFORMATION: Anti-galectin-1 siRNA human

<400> SEQUENCE: 1
gcugccagau ggauacgaa                                                19

<210> SEQ ID NO 2
<211> LENGTH: 21
<212> TYPE: RNA
<213> ORGANISM: Artificial Sequence
<220> FEATURE:
<223> OTHER INFORMATION: Anti-galectin-1 siRNA human
<220> FEATURE:
<221> NAME/KEY: misc_feature
```

<222> LOCATION: (20)..(21)
<223> OTHER INFORMATION: n is deoxythymidine

<400> SEQUENCE: 2
gcugccagau ggauacgaan n                                         21

<210> SEQ ID NO 3
<211> LENGTH: 21
<212> TYPE: RNA
<213> ORGANISM: Artificial Sequence
<220> FEATURE:
<223> OTHER INFORMATION: Anti-galectin-1 siRNA mouse
<220> FEATURE:
<221> NAME/KEY: misc_feature
<222> LOCATION: (20)..(21)
<223> OTHER INFORMATION: n is deoxythymidine

<400> SEQUENCE: 3
accugugccu acacuucaan n                                         21

<210> SEQ ID NO 4
<211> LENGTH: 21
<212> TYPE: RNA
<213> ORGANISM: Artificial Sequence
<220> FEATURE:
<223> OTHER INFORMATION: scrambled Anti-galectin-1 siRNA mouse
<220> FEATURE:
<221> NAME/KEY: misc_feature
<222> LOCATION: (20)..(21)
<223> OTHER INFORMATION: n is deoxythymidine

<400> SEQUENCE: 4 ggaaauccccc caacagugan n                                        21

<210> SEQ ID NO 5
<211> LENGTH: 20
<212> TYPE: DNA
<213> ORGANISM: Artificial Sequence
<220> FEATURE:
<223> OTHER INFORMATION: mouse Galectin-1 forward primer

<400> SEQUENCE: 5
caatcatggc ctgtggtctg                                           20

<210> SEQ ID NO 6
<211> LENGTH: 22
<212> TYPE: DNA
<213> ORGANISM: Artificial Sequence
<220> FEATURE:
<223> OTHER INFORMATION: mouse Galectin-1 reverse primer

<400> SEQUENCE: 6
ctgtaggcac aggttgttgc tg                                        22

<210> SEQ ID NO 7
<211> LENGTH: 26
<212> TYPE: DNA
<213> ORGANISM: Artificial Sequence
<220> FEATURE:
<223> OTHER INFORMATION: mouse Galectin-1 Taqman Probe

<400> SEQUENCE: 7
tcgccagcaa cctgaatctc aaacct                                    26

<210> SEQ ID NO 8
<211> LENGTH: 19
<212> TYPE: DNA

```
<213> ORGANISM: Artificial Sequence
<220> FEATURE:
<223> OTHER INFORMATION: mouse GAPDH forward primer

<400> SEQUENCE: 8
tcaccaccat ggagaaggc                                                 19

<210> SEQ ID NO 9
<211> LENGTH: 20
<212> TYPE: DNA
<213> ORGANISM: Artificial Sequence
<220> FEATURE:
<223> OTHER INFORMATION: mouse GAPDH reverse primer

<400> SEQUENCE: 9
gctaagcagt tggtggtgca                                                20

<210> SEQ ID NO 10
<211> LENGTH: 25
<212> TYPE: DNA
<213> ORGANISM: Artificial Sequence
<220> FEATURE:
<223> OTHER INFORMATION: mouse GAPDH Taqman Probe

<400> SEQUENCE: 10 atgccccat gtttgtgatg ggtgt                                           25
```

TREATMENT OF CENTRAL NERVOUS TUMOURS

REFERENCE TO SEQUENCE LISTING SUBMITTED VIA EFS-WEB

This application includes an electronically submitted sequence listing in .txt format. The contents of the electronic sequence listing (19893-31-2018-07-19-Sequence-Listing.txt; Size: 2,736 bytes; and Date of Creation: Jul. 19, 2018) is herein incorporated by reference in its entirety. The sequence listing is being electronically submitted via EFS-Web on Jul. 19, 2018.

FIELD OF THE INVENTION

The present invention relates to nanoparticles encapsulating siRNA for gene silencing of galectin-1 involved in tumour progression. The present invention further relates to the treatment of nervous brain tumours, such as glioblastoma multiforme (GBM) by intranasal delivery of such nanoparticles.

BACKGROUND OF THE INVENTION

Galectin-1 (Gal-1) is a naturally occurring galactose-binding lectin, which is overexpressed in glioblastoma multiforme (GBM). This lectin is associated with tumour progression, and a potent immune suppressor in the tumour micro-environment.

To inhibit Gal-1 in GBM, an effective therapy is required that reaches the central nervous system tumour, with limited systemic effects.

Gliomas are the most common type of intrinsic brain tumour, affecting 5-10 persons/100,000/year. Glioblastoma (GBM) is the most frequent glioma of astrocytic origin categorized by the world health organization as a grade 4 tumour [Louis, D. N. et al. (2007) *Acta neuropathol.* 114, 97-109]. Current treatment modalities fail to rescue GBM patients. Optimal treatment regimen consists of maximal surgical resection, followed by chemo- and radiation therapy. This multimodal treatment results in a median overall survival of 14.6 months [Stupp, R. et al. (2009) *The lancet oncology* 10, 459-466]. The poor prognosis has provoked a quest for many novel treatments over the past years. However, very few have reached clinical efficacy.

The potential of immunotherapy as novel approach to further improve the survival of GBM patients has been explored. Immunotherapy will harness the patient's own immune system towards the GBM. In relapsed malignant glioma patients, a substantial though still modest amount of long term survivors was reported, surviving more than 24 months after reoperation and dendritic cell vaccination [De Vleeschouwer S. (2008) *Clin. Cancer Res.* 14, 3098-3104; De Vleeschouwer, S. (2012) *Cancer Immunol Immunother.* 61, 2105-2112]. In newly diagnosed GBM patients, a median survival of 18.3 months in case of an integrated postoperative radiochemoimmunotherapy approach was reported, and a two year survival rate of more than 42% of the patients according to long-term analysis data. Despite this clinical feasibility, the final outcome for many patients remains unchanged with immunotherapy. Consensus is arising that GBM tumours are very potent immune-evasive tumours, pre-disposed to circumvent immune targeting therapies [Weathers S. P. & Gilbert M. R. (2015) *J. Neuro oncol.* 123, 331-337; Grauer, O. M. et al. (2009) *Brain Pathol* 19, 674-693].

Currently, the mediators that create this immune-evasive tumour micro-environment are under intensive investigation. Galectine-1 (Gal-1) has been identified as a potent naturally occurring immune-suppressive molecule, preferentially upregulated in GBM [Le Mercier M. et al (2010) *Brain Pathol* 20, 17-27, Toussaint, L. G. 3rd et al. (2012) *Molecular cancer* 11, 32].

Galectine-1 can induce apoptosis in activated CD8+ T cells, antagonize T cell signaling and block pro-inflammatory cytokine secretion [Rubinstein, N. et al. (2004) *Cancer cell* 5, 241-251; Garin, M. I. et al. (2007) *Blood* 109, 2058-2065]. It was previously demonstrated in the GL261, murine glioblastoma model, that depletion of Gal-1 can increase the efficacy of DC-based immunotherapy [Verschuere, T. et al. (2014) *Int J Cancer.* 134, 873-884]. From these data, Gal-1 is considered a potent immune regulator (in GBM). Gal-1 is not only involved in the immune suppression for GBM progression, but also several other key features have been attributed to this lectin [Camby, I. et al. (2006) *Glycobiology* 161, 37R-157R]. Upregulation of Gal-1 is correlated with an increased motility of GBM cells. Via rearrangement of the actin skeleton, Gal-1 can introduce a migratory phenotype in GBM cells. Moreover, Gal-1 has been proven to promote the angiogenesis in the tumour-micro environment. Not only the GBM cells can over express Gal-1, but also the endothelial cells, associated with the tumour. Functioning as a modulator for vascular endothelial growth factor maturation, Gal-1 can promote vessel growth. Furthermore, Gal-1 has been discovered as a mediator in chemo-resistance of GBM cells towards temozolomide, the most commonly used chemotherapeutic agent in GBM. Gal-1 can regulate the endoplasmatic reticulum stress to promote cell survival under temozolomide treatment [Le Mercier, M. et al. (2008) *J. Neuropathol. Ex Neurol* 67, 456-469; Le Mercier, M. et al. (2008) *Toxicol appl. pharm.* 229, 172-183; Croci, D. O. et al. (2014) *Cell* 156, 744-758.] In summary, Gal-1 is a crucial mediator at the interface of many GBM promoting phenomena, and therefore an ideal candidate to target.

Many strategies have been used to target Gal-1. In particular small-molecules such as Davanat®, OTX-008 (Anginex) have proven effectiveness in various cancers [Astorgues-Xerri, L. et al. (2014) *Eur J Cancer* 50, 2463-2477. Besides small molecules, also antibodies have been designed to tackle Gal-1. Two major obstacles are met when suppressing Gal-1: the targeting of both the intra- and extracellular fraction of Gal-1, and the specificity of the suppression. Interfering with other galectines is still under debate, as some galectines might have tumour regressing properties. To fulfil these requirements, the design of RNA interference based molecules is a very attractive approach. Short double stranded small interfering RNA molecules (siRNA) can be loaded into the RNA induced Silencing Complex (RISC complex), and selectively destroy the mRNA encoding Gal-1 [Schutze N. (2004) *Mol. cell endocrinol.* 213, 115-119]. Several papers have already demonstrated the efficacy of siRNA targeting Gal-1 in GBM cells [Le Mercier et al. 2008, both cited above]. Although efficacy of siRNA is seldom an issue, reaching a critical concentration at the tumour site is a major point of concern. The most attractive method mentioned in literature is to reach the GBM tumour via intraventricular injection where the siRNA molecules are infused with an osmotic mini-pump [Thakker, D. R. et al. (2004) *Proc Natl Acad Sci USA* 101, 17270-17275]. In a clinical setting, convection enhanced delivery systems are used for intracerebral injections in the context of brain tumours [Debinski, W.& Tatter, S. B. (2009) *Exp. Rev.*

Neurother. 9, 1519-1527]. Even with promising clinical outcomes, complications are inherent with this invasive technique. Infections, haemorrhages, wound healing problems and unreliable distribution volumes are often observed. In particular for drugs that need to be administered chronically on a long term, CED seems unattractive.

In recent years, a mounting body of evidence has accumulated that the intranasal pathway might represent a non-invasive alternative administration method [Illum, L. (2000) *Eur. J. Pharm. Sci.* 11, 1-18; Mistry, A. et al. (2009) *Int J Pharm.* 379, 146-157]. The intranasal transport has been described as a direct pathway from the nasal cavity towards the central nervous system. Transport of molecules along this pathway involves extra- and transcellular transport through the olfactory and respiratory mucosal epithelium of the nasal cavity. Perivascular and perineural transport along the (ilia olfactoria towards the olfactory bulbus and transport along the trigeminal nerves towards the brainstem seem to be of paramount importance Lochhead J. J.& Thorne, R. G. (2012) *Adv. Drug Deliv. Rev.* 64, 614-628. From there, a rapid spread into the CNS can occur. Direct transport from the nose to the brain beholds many advantages such as: better patient compliance through self-delivery, avoiding (too much) systemic absorption, and circumventing the blood-brain barrier (BBB) [Groothuis, D. R. (2000) *Neuro Oncol.* 2, 45-59]. This barrier cannot be crossed without high lipophilicity, or receptor-targeting e.g. transferrin and high expression of efflux-pump will avoid passage. Successful exploitation of the intranasal pathway will open a window of opportunity for many therapeutic molecules to treat GBM and other brain diseases [Kim, I. D. et al. (2012) *Mol. Ther.* 20, 829-839; Hashizume, R. et al. (2008) *Neuro-oncol.* 10, 112-120]. A literature overview describes the pharmaceutical aspects to further enhance the nose-to-brain transport [van Woensel, M. et al. (2013) *Cancers* 5, 1020-1048], with comments on the design of pharmaceutical formulations that improve the transport, protect the active drug, and thereby increase the overall bio-availability in the CNS of the active compound. In this respect, nanoparticulated formulations could offer an interesting new versatile platform. For improvement of the nose-to-brain transport, chitosan nanoparticles are gaining interest rapidly. Chitosan is a β-(1-4)-linked D-glucosamine and N-acetyl-D-glucosamine molecule, which are linked via glycosidic bonds [Bernkop-Schnurch, A. & Dunnhaupt, (2012) *Eur. J. Pharm. Biopharm.* 81, 463-469]. As a biodegradable, biocompatible, mild immunogenic, and little toxic polymer, chitosan presents ideal characteristics that are necessary for a future pharmaceutical use in humans. Moreover, with mucoadhesive and permeation-enhancing properties, this excipient seems an ideal candidate to further enhance the nose-to-brain transport. Chitosan promotes permeation by transiently opening the tight junctions in between epithelial cells [Bonferoni, M. C. et al. (2009) *Expert Opin. Drug Deliv.* 6, 923-939; Davis, S. S. & Illum, L. (2003) *Clin. Pharmacokinet.* 42, 1107-1128; Soane, R. J. et al. (2001) *Int. J. Pharm.* 217, 183-191]. Production processes of chitosan nanoparticles are widely described. Ionic gelation is one of the most popular methods due to the ease of manufacture, and the avoidance of harmful reagents. Chitosan has also been widely investigated for its transfection potential, in particular for siRNA delivery in the cytosol due to the endosomal escape [Katas, H. & Alpar, H. O. et al. (2006) *J. Control. Release* 15, 216-225].

Danhier et al. (2015) *Int. J. Pharm.* 481, 154-161, disclose anti-galectin-1 and anti-EGFR siRNA loaded lipid-chitosan particles made from chitosan with a Mr of 5 kDa.

U.S. Pat. No. 7,964,575 discloses the use of anti-galectin-1 targeted siRNA for the treatment of cancer and discusses delivery via nasal inhalation, without further on particles for delivery.

Le Mercier et al. (2008)*J. Neuropathol. Exp. Neurol.* 67, 456-469 disclose the administration of anti-galectin-1 siRNA to the brain via osmotic minipumps.

Le Mercier et al. (2008) *Toxicol. Appl. Pharmacol.* 229, 172-183 discloses the transfection of Galectin siRNA in human tumour cells which are subsequently implanted in mice.

Van Woensel (2013) *Cancers* 5, 1020-1048, reviews formulations for intranasal delivery, and discusses chitosan nanoparticles with pharmaceutical active compounds.

US20130337067 discloses nanoparticles with small Mr (7-10 kDa) for intranasal delivery to the brain and with larger Mr (50 to 190 kDa) for intraperitoneal delivery.

US20110033547 discloses various types of chitosan particles, without guidance for specific application routes.

Malhotra (2013)*J Pharmacol.* 2013, article 812387 discloses chitosan particles with chitosan of 10 kDa for intranasal delivery.

Malhotra 2013 equally discloses chitosan particles of 5-10 nm made from chitosan with Mr 20 kDa.

SUMMARY OF THE INVENTION

The present invention relates to new formulations containing nanoparticles encapsulating siRNA for the use of RNAi technology for gene silencing of galectin-1 involved in tumour progression. More in particular the present invention relates to chitosan nanoparticles encapsulating anti-galectin1 siRNA molecules, wherein said nanoparticles are suitable for the delivery of said siRNA molecules to the brain following intranasal administration. Nanoparticles according to the present invention are particularly suited for the treatment of brain tumours, more particularly for treating central nervous tumours, in particular glioblastoma multiforme (GBM).

One aspect of the invention relates to chitosan nanoparticles comprising siRNA targeting Galectin 1 (anti-Gal1 siRNA) for use in the treatment of central nervous tumours, such as glioblastoma multiforme, wherein the nanoparticles are administered via intranasal delivery, and wherein the chitosan molecules in the nanoparticles have a Mr of between 30 and 200 kDa, of between 30 and 100 kDa, between 30 and 60 kDa, between 45 and 55 kDa.

Typically, the molecules are cross-linked via sodium tripolyphosphate.

Generally, the anti-Gal1 siRNA comprises a nucleic acid sequence with at least 80% sequence identity to the nucleic acid sequence 5' GCUGCCAGAUGGAUACGAA3' (SEQ ID NO: 1).

In typical embodiments, the hydrodynamic diameter (z-average) of the particles is between 100 and 200 nm.

In typical embodiments the poly-dispersity index of the particles is between 0.15 and 0.40.

In typical embodiments at least part of the chitosan molecules carry one or more poly-ethylene glycol units, or one or more galactose units.

The nanoparticles can further comprise a lyoprotectant, such as sucrose or trehalose.

Another aspect of the invention relates to methods for the treatment of central nervous tumours in a patient, comprising the step of administering to the patient via intranasal delivery an affective amount of chitosan nanoparticles comprising siRNA compounds targeting Galectin 1 (anti-Gal1 siRNA), wherein the chitosan molecules in the nanoparticles have a Mr of between 30 and 200 kDa.

The embodiments mentioned above for the second medical use claim are equally applicable to these methods of treatment.

Another aspect of the invention relates to pharmaceutical compositions for nasal delivery comprising Chitosan nanoparticles comprising siRNA compounds targeting Galectin 1 (anti-Gal1 siRNA), and an excipient suitable for intranasal delivery, wherein the chitosan molecules in the nanoparticles have a Mr of between 30 and 200 kDa.

The embodiments mentioned above for the second medical use claim are equally applicable to these pharmaceutical compositions.

Another aspect of the invention relates to intranasal delivery systems comprising the above pharmaceutical compositions.

Another aspect of the invention relates to methods for the preparation of the chitosan nanoparticles. These methods comprise the steps of:
1) dissolving chitosan polymers having a molecular weight between 30 and 200 kDa in an acetic solution;
2) dissolving anti-Gal1 siRNA in a solution of a negatively charged compound suitable for crosslinking chitosan polymers;
3) adding the solution comprising the anti-Gal1 siRNA and the compound for crosslinking to solution of chitosan polymers of step 1) while stirring or mixing the combined solutions in order to obtain the formation of suspended chitosan nanoparticles comprising anti-Gal1 siRNA;
4) collecting the chitosan nanoparticles using filtration, centrifugation or other suitable technique for isolating the suspended nanoparticles.

Herein the anti-Gal1 siRNA typically comprises a nucleic acid sequence with at least 80% sequence identity to the nucleic acid sequence 5'GCUGCCAGAUGGAUACGAA3' (SEQ ID NO:1).

The chitosan polymers have a molecular weight between 30 and 60 kDa, or between 45 and 55 kDa.

Typically, the degree of de-acetylation of the chitosan polymers is at least 70%.

Generally, between 30 and 60 μg anti-Gal1 siRNA is added per mg of chitosan.

The crosslinking compound is typically sodium tripolyphosphate.

Typically the chitosan to sodium tripolyphosphate weight ratio is between 2.5 and 3.0.

In specific embodiments the chitosan nanoparticles collected in step 4) are combined with a lyoprotectant and are subsequently freeze dried. Examples of lyoprotectants are sucrose or trehalose.

In this study, we report for the first time how maximally concentrated chitosan nanoparticles can deliver siRNA molecules into the central nervous system within hours after intranasal administration. These nanoparticles can encapsulate siRNA targeting Gal-1 to a high percentage, and protect them from degradation. Moreover, successful delivery of anti-Gal-1 siRNA results in a decreased expression of Gal-1 in both murine and human GBM cells. The present invention shows that the intranasal pathway is an effective transport route to deliver Gal-1 targeting siRNA therapies in the treatment of GBM.

It is an object of the present invention to provide chitosan nanoparticles that encapsulate and protect siRNA specific for Gal-1 targeting to the brain following intranasal administration. We examined their transfection potential in murine and human GBM cell lines. Furthermore, we evaluated the formulation to open the tight junctions on an epithelial layer. We also investigated the rapid occurrence of the fluorophore-tagged siRNA-formulation in the central nervous system after intranasal instillation, with a preferential distribution at the olfactory bulbus, and the hindbrain; suggestive for partial transport via the olfactory and trigeminal pathway.

The present invention discloses:
1. Chitosan nanoparticles comprising siRNA compounds targeting Galectin 1 (anti-Gal1 siRNA) for use in the treatment of central nervous tumours, in particular glioblastoma multiforme.
2. The chitosan nanoparticles according of statement 1 wherein said anti-Gal1 siRNA comprises a nucleic acid sequence with at least 70% sequence identity to the nucleic acid sequence 5'GCUGCCAGAUGGAUACGAA3' [SEQ ID NO:1]. Preferably, said anti-Gal1 siRNA has a nucleic acid sequence with at least 80%, for instance at least 85%, 90% or 95% sequence identity to the nucleic acid sequence 5'GCUGCCAGAUGGAUACGAA3' [SEQ ID NO:1].
3. The chitosan nanoparticles according to statement 1 or 2 wherein the hydrodynamic diameter (z-average) of said particles varies between 100 and 300 nm, preferably between 100 and 200 nm.
4. The chitosan nanoparticles according to statements 1 to 3 wherein the poly-dispersity index of said particles varies between 0.15 and 0.40.
5. The chitosan nanoparticles according to statements 1 to 4 wherein at least part of the chitosan molecules carry one or more poly-ethylene glycol units.
6. The chitosan nanoparticles according to statements 1 to 4 wherein at least part of the chitosan molecules carry one or more galactose units.
7. A pharmaceutical preparation comprising the chitosan nanoparticles according to statements 1 to 6 said preparation further comprising a lyoprotectant.
8. The pharmaceutical preparation according to statement 7 wherein said lyoprotectant is sucrose and wherein the chitosan nanoparticle to sucrose ratio typically varies between 1/2 to 1/16, or between 1/4 and 1/12, such as about 1/8.
9. The pharmaceutical preparation according to statement 7 wherein said lyoprotectant is trehalose and wherein the chitosan nanoparticle to sucrose ratio typically varies between 1/8 to 1/28, or between 1/10 and 1/20, such as about 1/14.
10. The pharmaceutical preparation according to statements 8 or 9 wherein said pharmaceutical preparation comprises excipients suitable for the nasal administration thereof.
11. An intranasal delivery system comprising the chitosan nanoparticles according to any of the statements 1 to 6.
12. A method for the preparation of the chitosan nanoparticles according to statements 1 to 6, said method comprising the steps of:
i. dissolving chitosan polymers having a molecular weight between 30 and 200 kDa in an acetic solution;
ii. dissolving anti-Gal1 siRNA in a solution of a negatively charged compound suitable for crosslinking chitosan polymers;
iii. adding the solution comprising the anti-Gal1 siRNA and the chitosan crosslinking compound to the chitosan solution of step (i) while stirring or mixing said combined solutions in order to obtain the formation of suspended anti-Gal1 siRNA-containing chitosan nanoparticles;
iv. collecting said anti-Gal1 siRNA-containing chitosan nanoparticles using filtration, centrifugation or other suitable techniques for isolating the suspended nanoparticles.

13. The method according to statement 12 wherein said chitosan polymers have a molecular weight between 30 and 60 kDa.

14. The method according to statements 12 or 13 wherein the degree of de-acetylation of said chitosan polymers is at least 70%.

15. The method according to statements 12 to 14 wherein between 30 and 60 µg anti-Gal1 siRNA is added per mg of chitosan.

16. The method according to statements 12 to 15 wherein said chitosan crosslinking compound is sodium tripolyphosphate.

17. The method according to statement 16 wherein the chitosan to sodium tripolyphosphate weight ratio is between 2.5 and 3.0.

18. The method according to statements 12 to 17 wherein the chitosan nanoparticles collected in step (iv) are combined with a lyoprotectant and are subsequently freeze dried.

19. The method according to statement 18 wherein said lyoprotectant is sucrose.

20. The method according to statement 18 wherein said lyoprotectant is trehalose.

Nanoparticles for use in transnasal delivery should on the one hand be large enough to shield siRNA from degradation and on the other hand be small enough to easily be transported from the nasal cavity to the brain, and to release its drug load sufficiently fast from the particle. Contrary to the current opinion on nanoparticles for transnasal drug delivery, wherein small nanoparticles are used with low Mr chitosan, the examples of the present invention illustrate that particles of larger chitosan Mr are still efficient, indicating that the particles arrive at the target site, that RNAse degradation is tolerable, and that siRNA is sufficiently fast released.

As a consequence the particles as disclosed in the present invention can be equally used for siRNA against other target genes in the brain. In addition the tumour mouse model as described in the examples is suitable for further optimising physical parameters of chitosan nanoparticles.

DESCRIPTION

Legends to the Figures

FIGS. 1A and 1B. Gal-1 expression in cells cultured in presence of anti-Gal-1 loaded nanoparticles prepared using 20 kDa or 50 kDa chitosan. (A) Picture of a Western Blot analysis of Gal-1 in cell lysates of GL261 cells 4 and 7 days following transfection using Gal-1 siRNA loaded nanoparticles produced with 20 kDa and 50 kDa chitosan, respectively. (B) This experiment was repeated 3 times, and quantified by ImageJ analysis.

FIG. 2. Loading capacity and protection from RNases in chitosan nanoparticles comprising chitosan molecules having a 50 kDa MW. siRNA is incorporated to a very high percentage, with no visual migration of free siRNA; moreover siRNA was protected from RNases during different co-incubation times (3 h, 2 h, 1 h and 0.5 h). Free siRNA was rapidly degraded. CS NPs: Chitosan nanoparticles, SDS: Sodium dodecyl sulphate.

FIGS. 3A to 3F. Interaction of chitosan nanoparticles with GBM cells. Analysis on murine (A, B and C) or human glioblastoma cell line (D, E, F). Immunofluorescence pictures (presented in grayscale) of GL261 (A) cells and human primary GBM culture (D), with a respectively brightfield or DAPI as background, 2 h after incubation with nanoparticles. These pictures show a rapid attachment of the formulation on the cells (B) Relative Gal-1/GAPDH mRNA analysis on GL261 treated cells reveal a significant reduction of Gal-1 (black bar; with siRNA and white bar; without siRNA, expressed as mean with SD, two-way anova) (C) Western blot of treated GL261 cells at day 4 and 7 after transfection confirm on protein level the Gal-1 reduction (E) Quantification of six independent primary human GBM cultures at day 4 and 7 after transfection show the significant reduction of Gal-1 (n=6, paired t-test, one-tailed) (F) Example of one of the blots of a human primary GBM at day 4 and 7 after transfection. * p<0.05 and ** p<0.01

Figure 4:
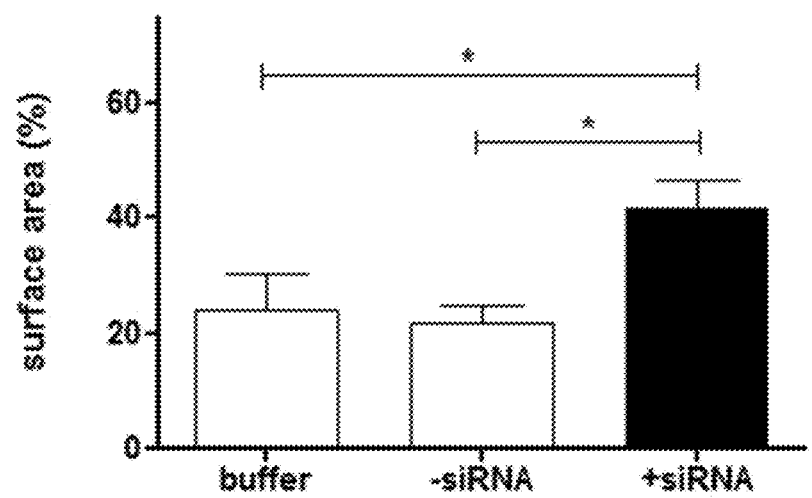
Figure 5A:
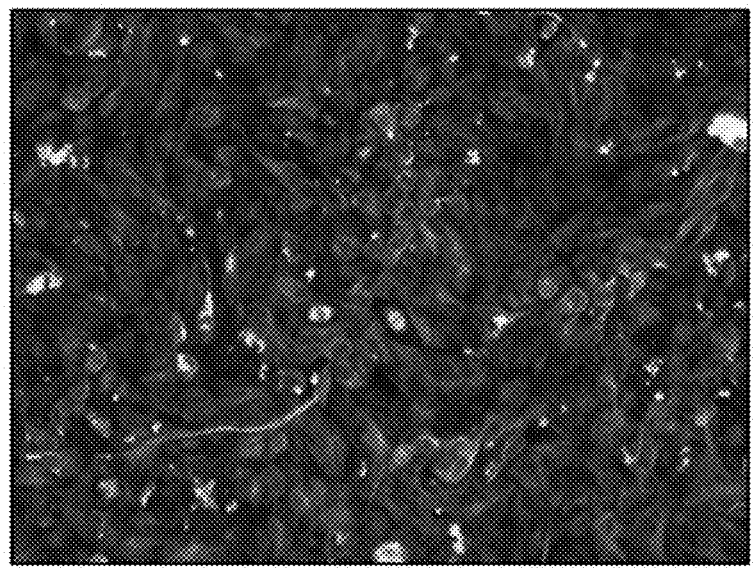
Figure 5B:
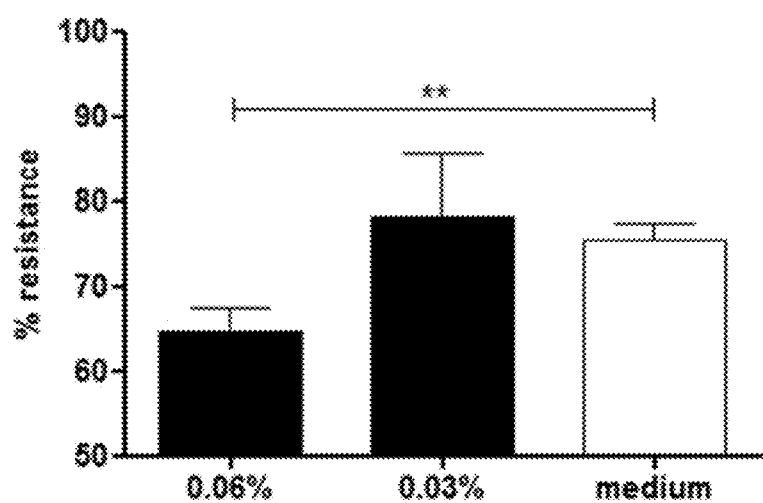
Figure 5C:
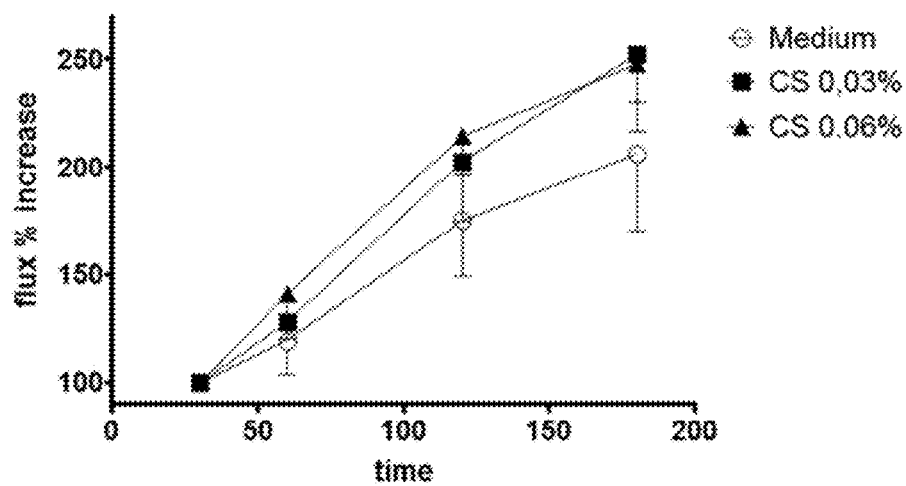
Figure 5D:
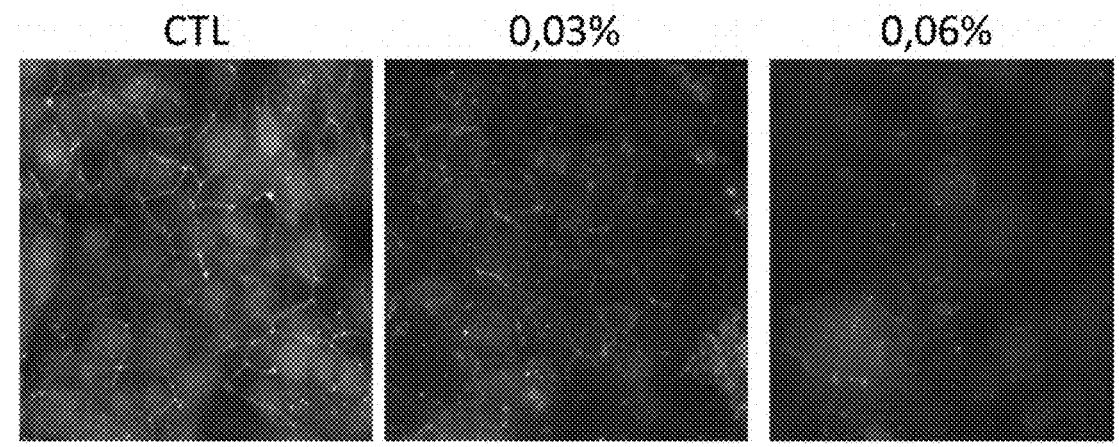

FIG. 4. Scratch wound assay for migration analysis on GL261 cells. Quantification of scratch area, 48 h after introducing the scratch shows that the Gal-1 reduced GL261 cells are less potent to migrate into the scratch (n=12, expressed as mean+SEM, one-way anova with Bonferroni's Multiple Comparison Test, calculated as % from time=0) *p<0.05

FIGS. 5A to 5D. Interaction of chitosan nanoparticles with epithelial cells. (A) Grayscale representation of immunofluorescence picture of a Calu-3 monolayer, nuclei: identifiable as dark grey dots in grayscale representation (original colour: blue), tubuline: not visible in grayscale (original colour: yellow), nanoparticles: identifiable as bright dots/areas in grayscale representation (original colour: green), 2 h after incubation displaying the rapid attachment (B) TEER measurement at 2 h after incubation with chitosan nanoparticles, indicates a significant transient decrease in resistance, corrected for the baseline TEER at time=0. (n=9, expressed as mean+SD, one way ANOVA with Dunn's Multiple Comparison Test) (C) FD4 passage over a Calu-3 monolayer, expressed as % flux increase over time, suggests an increased passage of FD4 after chitosan nanoparticles application (n=6, expressed as mean+SEM) (D) Immunofluorescence picture for localization of ZO-1, 2 h after incubation suggests a transient disturbing of tight junction (image presents grey scale of green channel corresponding to the ZO1 staining). ** p<0.01

Figure 6:
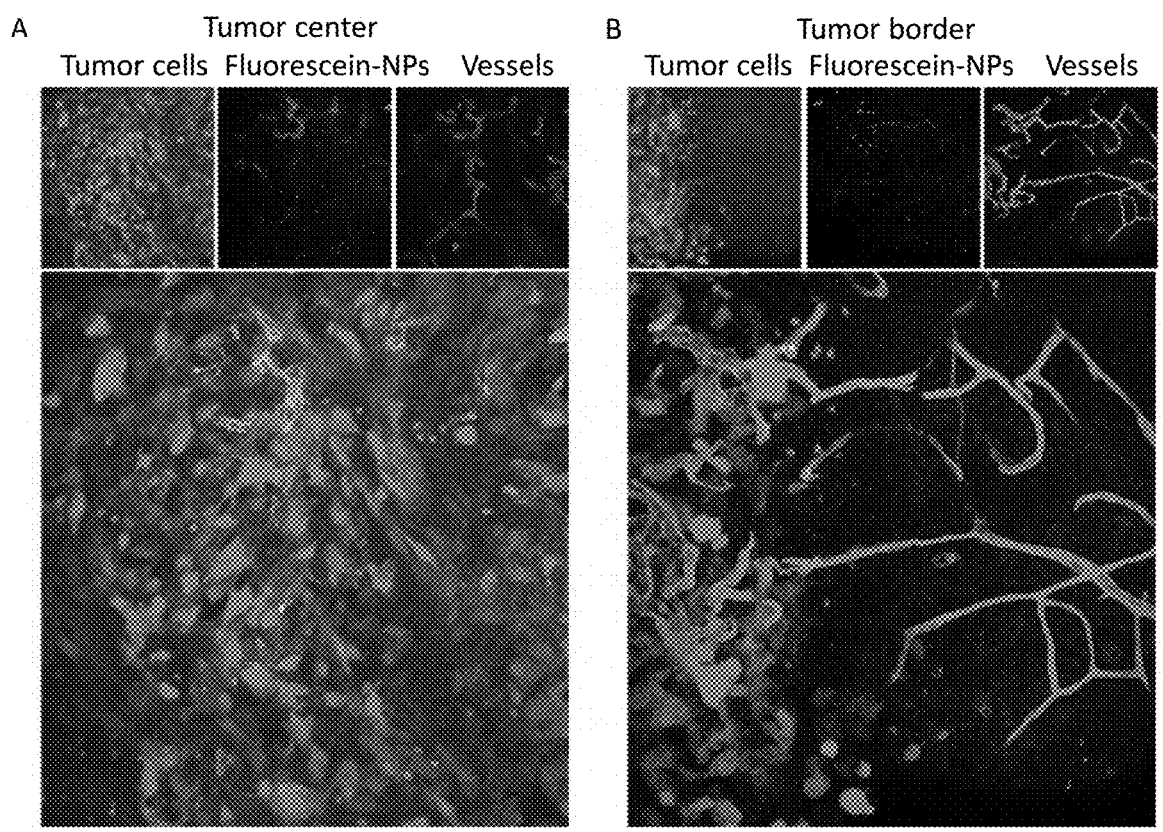

FIG. 6. Fluorescent microscopy of the distribution/local tropism in the tumour micro environment. (A) Confocal picture of treated mouse 4 h after the last administration fluorescein labelled siRNA loaded nanoparticles at the tumour centre of BFP-GL261 tumour; with the individual colour channels on top; this picture suggest a distribution via the systemic circulation, associated with some vessels. (B) Confocal picture of treated mouse 4 h after the last administration fluorescein labelled siRNA loaded nanoparticles at the tumour border of BFP-GL261 tumour; with the individual colour channels on top; this picture suggest a local enrichment in the tumour environment.

Figure 7A:
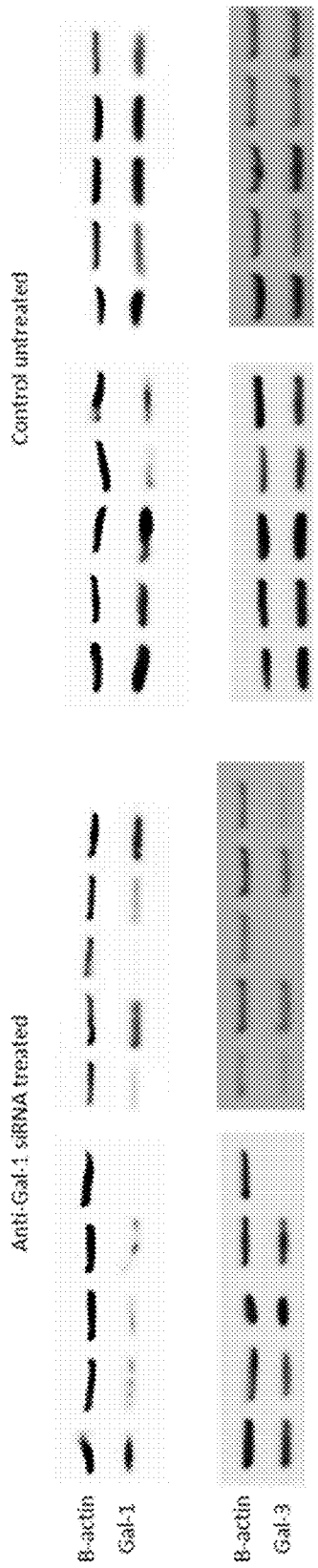
Figure 7B:
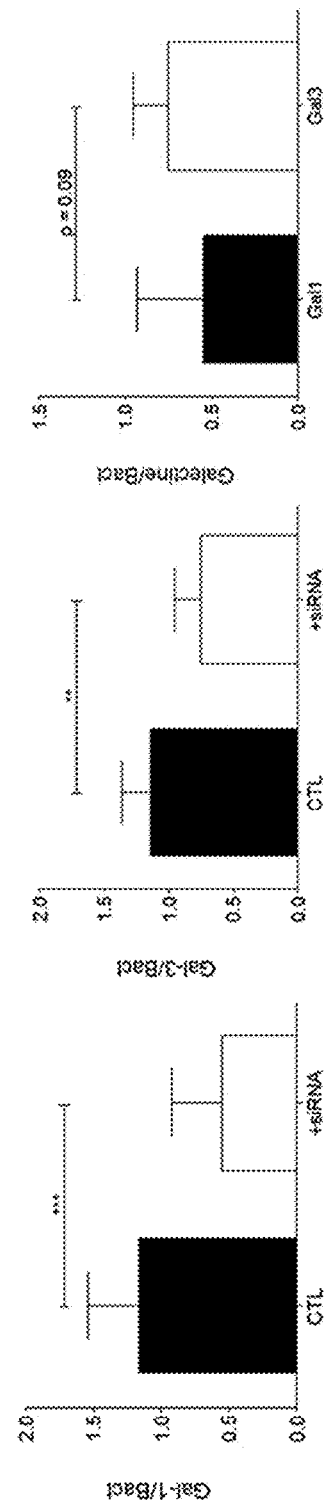

FIGS. 7A and 7B. Specific knockdown of Gal-1. (A) Western blot of mice treated with anti-Gal-1 therapy, or untreated. Blots were performed for Gal-1 and Gal-3 as an additional tumour associated protein(B) Quantification of western blot via ImageJ intensity calculation. This analysis reveals a specific knockdown of Gal-1 in treated mice, and to a lesser extent of Gal-3. (unpaired one tailed t-test; n=10/group;  p<0.01, * p<0.001, blots are show belong to two independent experiments)

Figure 8:
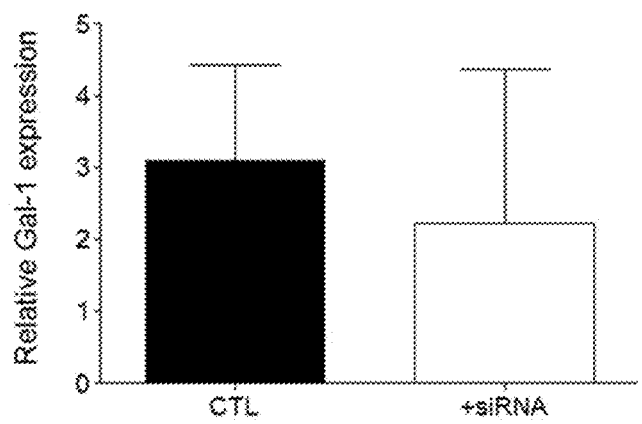

FIG. 8. Relative knockdown of Gal-1. (A) RT-qPCR analysis of mice treated with anti-Gal-1 therapy, or untreated. This analysis reveals a suggestion for a knockdown of Gal-1 in treated mice. (unpaired one tailed t test; n=10/group, p=0.14)

Figure 9:
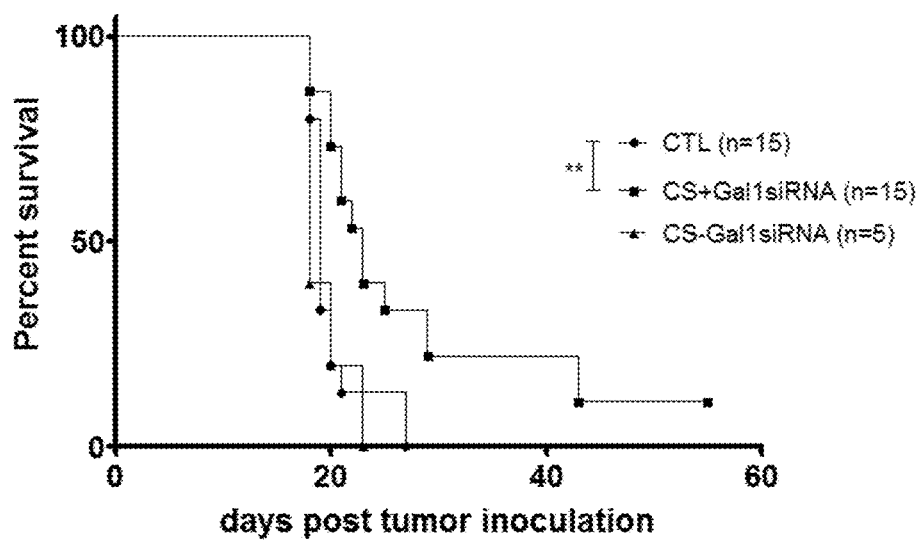

FIG. 9. Survival analysis after GL261 tumour inoculation. Mice were intracranially injected with $0.5 \times 10^6$ GL261 murine tumour cells. Subsequently, mice were left untreated, or treated with anti-Gal-1 siRNA loaded chitosan nanoparticles at day 5,8, 12 and 15 after tumour inoculation. Gal-1 reduction significantly increased the survival of treated mice (n=15/group, Log rank test, ** p<0.01)

Figure 10:
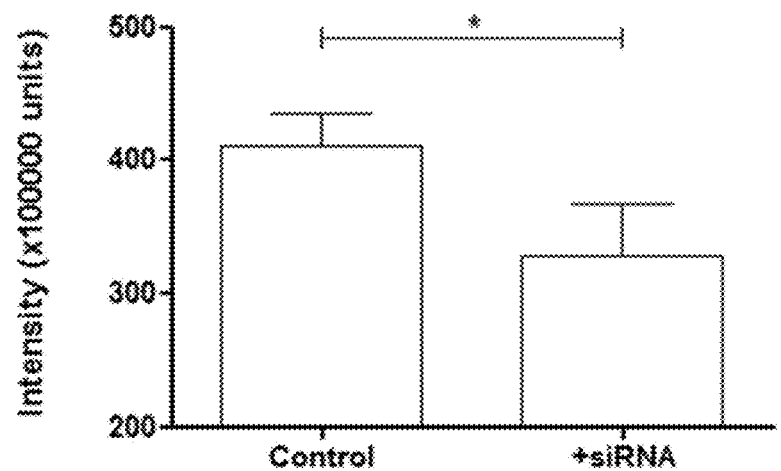
Figure 10:
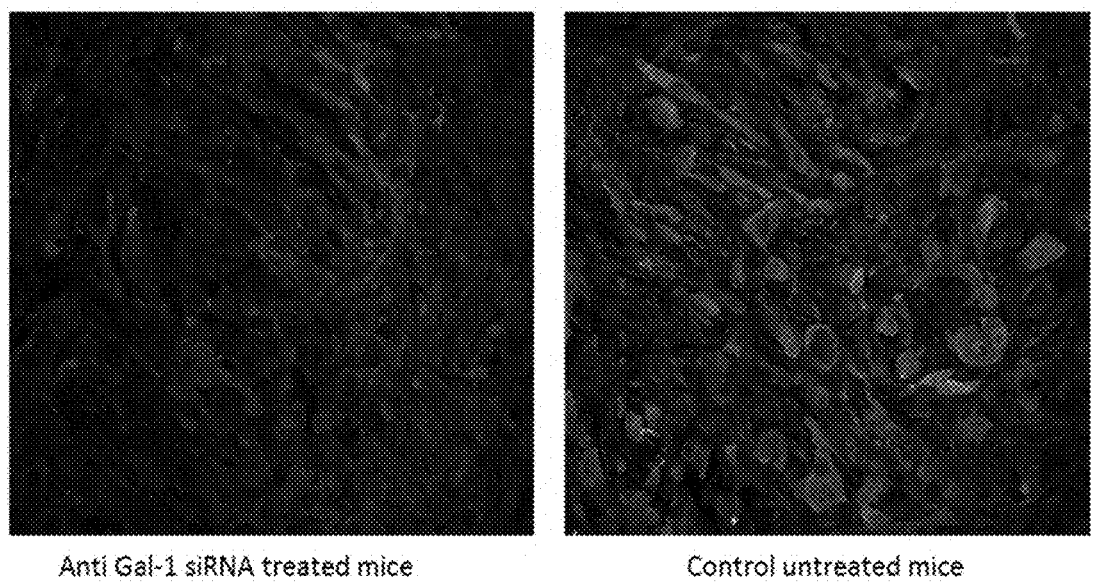

FIG. 10. Confirmation of knockdown of Gal-1 via immunofluorescence. (A) Quantification of 4 anti-Gal-1 siRNA mice versus 5 untreated control mice. (Mann-Whitney test; * p<0.05), (B) Greyscale pictures of representative immunofluorescence illustrations of a tumour area of a treated and untreated mouse, respectively.

DEFINITIONS

Within the context of the present invention 'chitosan' is a β-(1-4)-linked D-glucosamine and N-acetyl-D-glucosamine molecule, which are linked via glycosidic bonds. In the context of the present invention, Chitosan is prepared ionic gelation. Chitosan molecules used as starting material in the preparation of said nanoparticles have a molecular weight between 30 and 200 kDa, or between 30 and 100 kDa, such as between 30 and 60 kDa, or between 45 and 55 Kda (e.g. 50 kDa).

Within the context of the present invention 'chitosan nanoparticles' refers to nanoparticles for example prepared byionic gelation using a suitable crosslinking molecule, such as Sodium tripolyphosphate (TPP). The chitosan nanoparticles are used to encapsulate anti-Gall siRNA molecules. Encapsulation of siRNA molecules can for instance be obtained by pre-incubation of siRNA and TPP before nanoparticle formation. The nanoparticles according to the present invention typically have a hydrodynamic diameter between 100 and 300 nm, or between 100 and 200 nm. Further, the polydispersity index, being a measure for the size distribution of the nanoparticles typically varies between 0.15 and 0.40, more preferably between 0.2 and 0.30.

Chitosan particles can be "unmodified" particles or can be further modified with e.g. PEG or galactose.

Within the context of the present invention "anti-Gall siRNA" refers to an siRNA construct that silences the translation of Galectin-1 (see uniprot entry P09382 last modified on May 16, 2014 anti-Gall siRNA constructs have a nucleic acid sequence with at least 70%, 85%, 90%, 95%, sequence identity to the nucleic acid sequence 5' GCUGCCAGAUGGAUACGAA3' [SEQ ID NO:1] (e.g. 3, 2 or 1 difference in nucleotide sequence.

As illustrated in the examples of the present invention one siRNA against one gene has been used. It is envisaged that different siRNA against Galectin-1 can be used, and that in addition one or more siRNA against another gene involved in central nervous tumours can be used.

Within the context of the present invention the term "central nervous tumours" refers to any of the tumours classified by the WHO as described in Acta Neuropathologica, August 2007, 114(2), 97-109. The present invention relates in particular relates to tumours of neuroepithelial tissue, such as astrocytic tumours, more particular to glioblastoma tumours such as glioblastoma multiforme.

"Polydispersity index", [Ð] can refer to either molecular mass [ÐM] or degree of polymerization [ÐX]. It can be calculated using the equation DM=Mw/Mn, where Mw is the weight-average molar mass and Mn is the number-average molar mass. It can also be calculated according to degree of polymerization, where DX=Xw/Xn, where Xw is the weight-average degree of polymerization and Xn is the number-average degree of polymerization.

The size distribution of particles is described by the hydrodynamic diameter of such particles, wherein the statement "between x nm and y nm", indicates that within a population at least 60, 75, 80, 90 or 95% of the particles have hydrodynamic diameter within that range.

"Treatment" in the context of the present invention relates to any parameter that is indicative in an improvement of the health of the patient. In the context of the present invention it relates to parameters such as survival rate after treatment, partial or total reduction in size or mass of the tumour tissue, a decrease in complaints of the patient (such as seizure, nausea vomiting, headache, memory loss, hemiparesis, progressive memory deficit, change in personality, or neurological deficit).

"excipients for intranasal delivery" are described e.g. in US2013/0337067 and include pharmaceutically acceptable diluents, preservatives, solubilizers, emulsifiers, adjuvants and/or carriers. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, and detergents (e.g. Tween Tween 80™, Pluronic F68™, bile acid salts). The pharmaceutical composition can comprise pharmaceutically acceptable solubilizing agents (e.g. glycerol, polyethylene glycol), anti-oxidants (e.g. ascorbic acid, sodium metabisulfite), preservatives (e.g. thimerosal, benzyl alcohol, parabens), bulking substances or tonicity modifiers (e.g. lactose, mannitol).

"intranasal delivery" refers to extra- and transcellular transport through the olfactory and respiratory mucosal epithelium from the nasal cavity to the brain. This physiological process is described in detail in Van Woensel et al. (2013), cited above. Devices for intranasal delivery are commercially available and are known under the trade names Vianase (Kurve Technologies, USA) DirectHaler (Denmark) or OptiMist (Norway).

siRNA (small interfering RNA) refers to short RNA molecules for gene knockdown which bind to mRNA of a target gene. They are typically between 20 and 24 nucleotides and can be administered as single strand molecules, but also as longer double stranded molecules (e.g. hairpin RNAs) which are processed in the body to single stranded molecules.

EXAMPLES

Material and Methods

Chitosan (Heppe Medical chitosan, Germany) was obtained with a well-defined molecular weight of 50 kDa, measured as 10 mPas viscosity as 1% in 1% acetic acid at 20° C. Degree of de-acetylation amounted 85.2%. Sodium tripolyphosphate (TPP), sucrose, sodium dodecyl sulfate (SDS) and FITC-dextran (FD4) were purchased from Sigma-Aldrich (238503, S 9378, 71727, 46944, St. Louis, USA). Anti-Gal-1 (human: 5'GCUGCCAGAUG-GAUACGAAdTdT3' [SEQ ID NO: 2], mouse: 5' ACCU-GUGCCUACACUUCAAdTdT3' [SEQ ID NO: 3] and scrambled siRNA (5'GGAAAUCCCC-CAACAGUGAdTdT3' [SEQ ID NO: 4] was purchased from GE Dharmacon, and if necessary labelled with fluorescein or 5'-dye 547 (custom design, Lafayette, USA).

Methylcholanthrene-induced murine C57BL/6J syngeneic GL261 glioma cells were kindly provided by Dr. Eyupoglu (University of Erlangen, Germany) and were cultured as described in Maes, W. et al. (2013) *Clin. & Dev.l Immunol.*, 2013 Article ID 952469.

In some experiments, GL261 cells were used that expressed blue fluorescent protein (BFP). Via lentiviral transduction, BFP production was inserted.

Primary glioblastoma cultures were obtained from resection specimen from patients after informed consent. In brief, tumour specimen were dissociated via 30' incubation with collagenaseD and DNase at 37° C. Subsequently, mononuclear cells were isolated on a Ficoll gradient (Lymphoprep, AxisShield, Norway), and cells were seeded in RPMI medium under 20% FCS conditions. The Calu-3 cell line was purchased from the American Type Culture Collection, ATCC HTB-55, and cultivated under the same conditions as described in Vllasaliu, D. et al. (2010) *Int. J. Pharm.* 400, 183-193.

Eight-to-ten week-old female C57BL/6J mice were purchased from Harlan (Horst, The Netherlands). The mice were maintained under conventional pathogen-free conditions. All experiments were approved by the bioethics committee of the KU Leuven, which follows international guidelines.

Preparation of Nanoparticles.

Nanoparticles were obtained by ionic gelation. Chitosan polymers were positively charged by dissolution in 0.1 M acetic acid buffer pH 4.5. TPP was chosen as crosslinker to interconnect the chitosan polymers. Due to the negative charge of both TPP and the phosphates of siRNA, chitosan nanoparticles were spontaneously formed [Katas & Alpar, cited above]. TPP (1 mg/ml) was added to chitosan (0.7 mg/ml) under constant stirring, with a chitosan to TPP weight ratio of 2.625/1. Encapsulation of siRNA molecules was achieved by pre-incubation of siRNA and TPP before nanoparticle formation, with a total amount of 24 µg siRNA for 1 ml nanoparticles. The nanoparticles were stirred for 30' at room temperature. Subsequently, particles were collected via ultracentrifugation at 40000×g for 20 min. The pellet was dissolved in 0.075M acetic acid buffer pH 4.5 and the supernatant was centrifuged again twice. The three pellets were pooled and freeze dried with sucrose as a lyoprotectant with a nanoparticle/lyoprotectant weight ratio of 1/8.

Characterization of Nanoparticles: Size, Charge and Stability.

The hydrodynamic diameter (Z-average), the polydispersity index (PDI) and the zeta potential of the nano-sized formulation were determined by dynamic laser scattering and laser Doppler electrophoresis using a Zetasizer nano ZS (Malvern Instruments, UK). The measurements were made after a 1:10 dilution in 0.075M acetic acid buffer pH 4.5 at 37° C. in triplicate. Stability of the nanoparticles was assessed by conservation at 4° C. in a desiccator.

Characterization of Nanoparticles: siRNA Encapsulation Efficiency.

The percentage siRNA encapsulation was determined by using the SYBR green assay [Pardridge, W. M. (2007) *Drug Discov Today* 12, 54-61]. This selective dye can only emit fluorescence upon binding into the helix of siRNA molecules. Particles were prepared and stirred for 30'. Subsequently, the particles were incubated with SYBR green for 30'. Free siRNA was used to prepare a standard curve and detected by fluorescence plate reader in a black 96-well plate (Nunc), at 480 nm (ex) and 520 nm (em). As a positive control 0.1% SDS was added to break ionic complexations. In parallel, the percentage free siRNA was also evaluated in the supernatant after ultracentrifugation by measuring the fluorescent unbound siRNA.

Characterization of Nanoparticles: Protection Against siRNA Degradation.

Protection of siRNA degradation by ribonucleases (RNases) was assessed by a gel retardation assay. In brief, the chitosan nanoparticles were incubated with 0.07% recombinant RNaseA (12019-021, Life Technologies) at 37° C. Next, the particles were loaded onto a 4% agarose gel that was prepared with Tris/borate/EDTA buffer (10×Ultrapure TBE, Life Technologies). For better visualization, particles were dissociated by 0.1% SDS before loading them onto the gel. An equal amount of free siRNA was also incubated with RNaseA, and loaded onto the gel. Migration of siRNA was forced by applying 55 V for 2 h. Visualization was achieved by staining the gel with ethidium bromide for 30'.

Interaction with Glioma Cells.

Both murine GL261 glioma cells and human primary culture glioblastoma cells were grown on a glass cover slip. Next, particles enloaded with fluorescein-tagged siRNA were incubated with the cells. At regular time intervals, the glass cover slips were washed, and fixed in 4% paraformaldehyde for 10'. In case of the human primary cultures, an additional immunofluorescence staining was performed which stained their nuclei with 4',6-Diamidino-2-phenylindole dihydrochloride (DAPI, sigma).

Transfection Assay.

GL261 cells and human primary glioblastoma cells were cultivated up to a density of maximum 60% of full confluence. Chitosan nanoparticles were added in serum-free culture conditions overnight up to a final siRNA concentration of 20 nM. The cells were washed extensively with PBS and put back into serum condition media. From this cell population, glioblastoma cells were seeded for the assessment of the transfection efficiency through time.

Transfection Assay: mRNA.

Treated cells were harvested at different days post-transfection, and RNA was isolated (Miniprep, Qiagen) and quality controlled via spectrophotometer (Nanodrop, Thermo scientific). Subsequently, a cDNA template was created via a reverse polymerase reaction (Superscript II, Invitrogen) and a Real-Time quantitative Polymerase Chain Reaction (RT-qPCR) was performed on these samples. Following primer pairs were used for detection of Galectin-1 and GAPDH as a housekeeping gene (Table 1). The ratio of Gal-1/GAPDH in untreated cells was used as the 100% baseline.

TABLE 1

Primer pairs and probes for RT-qPCR. Sequences for Gal-1 and GAPDH to quantify the amount of murine mRNA encoding for Gal-1.

| Gene | Primer/probe | sequence | SEQ ID NO: |
|---|---|---|---|
| Galectin-1 | forward | caa tca tgg cct gtg gtc tg | 5 |
| | reverse | ctg tag gca cag gtt gtt gct g | 6 |
| | Taqman Probe | tcg cca gca acc tga atc tca aac ct | 7 |

TABLE 1-continued

Primer pairs and probes for RT-qPCR. Sequences for Gal-1 and GAPDH
to quantify the amount of murine mRNA encoding for Gal-1.

| Gene | Primer/probe | sequence | SEQ ID NO: |
|---|---|---|---|
| GAPDH | forward | tca cca cca tgg aga agg c | 8 |
|  | reverse | gct aag cag ttg gtg gtg ca | 9 |
|  | Taqman Probe | atg ccc cca tgt ttg tga tgg gtg t | 10 |

Transfection Assay: Protein.

Treated cells were harvested at different days post-transfection, and proteins were isolated (Tissue Protein Extraction Reagent, Life Technologies). Protein concentration was determined via a colourimetric assay (BCA kit, Life Technologies). Equal amounts of total protein were separated by sodium dodecyl sulfate/polyacrylamide gel electrophoresis and transferred to a polyvinylidene difluoride membrane. Membranes were incubated overnight with primary antibody: rabbit anti-Galectin-1 (1:1000; Peprotech, Quebec, Canada). As a protein-loading control, all blots were stained with rabbit anti-β-Actin (1:5000; Abcam). Secondary antibody used was peroxidase-conjugated goat anti-rabbit IgG (1:5000; Dako). Visualization was performed via chemiluminescence (western lightening, Perkin Elmer). Quantification of the bands was performed with ImageJ software.

Transfection Assay: Migration Assay.

Four days after transfection, GL261 cells were plated into 6 well plates. Cells were allowed attachment overnight, and grown to a monolayer. With a 200 µl pipet tip, a scratch was introduced, without affecting the plate coating. Three independent pictures were taken from this scratch, and the experiment was performed in quadruplet. Pictures were taken at 12, 23 and 48 h after introducing the scratch. Surface area was calculated via software (ImageJ) and calculated as % compared to the baseline surface area.

Epithelial Barrier Integrity.

Calu-3 cells were seeded at 250,000 cells/insert grown to a monolayer on 12 well transwell insert (0.4 µm translucent polyester, Greiner). After 14 days a monolayer was formed that displayed a stable transepithelial electrical resistance (TEER). To confirm the tight monolayer, and the adherence of the formulation onto the monolayer, an immunofluorescence staining was performed. After fixation, the cells were permeabilized in a Tris/NaCl/Tween buffer (TNT), with triton-X 100 and rabbit anti-tubulin (1/100, ab15246, Abcam) primary antibody was added. Cells were washed thoroughly and donkey anti-rabbit IgG—alexa fluor 555 was added (1/200, A31572, Life Technologies). Afterwards DAPI was added for nuclei staining. In case of tight-junction assessment, we used anti ZO-1 antibody as primary antibody (1/100, 33-910, Life technologies). TEER measurements were obtained by using EVOM volthommeter (World Precision Instruments) configured with a pair of chopstick electrodes. To evaluate the capacity of chitosan nanoparticles to transiently disturb the epithelial barrier integrity, the chitosan nanoparticles were incubated on a monolayer of Calu-3 cells. Baseline TEER measurements were expressed as 100%. In addition, macromolecular permeability was measured as alternative parameter to evaluate the integrity of the epithelial barrier. FD4 was used as hydrophilic model drug, most likely to travel in the paracellular spaces.

In Vivo Administration and Assessment.

For in vivo distribution studies, mice were anesthetized with isoflurane 3% during the administration period. Each mouse was administered with 8 times 3 µl drops with a time interval of 3' between every drop. Administrations were performed for either 1 time or three times during 3 consecutive days, and 4 h after the last administration, mice were sacrificed by intraperitoneal injection of Nembutal, and perfused with cold PBS followed by perfusion with 4% formaldehyde. Nasal mucosa and brains were carefully isolated, and fixed for an additional 12 h with 4% formaldehyde. Nasal mucosa was prepared for sectioning by scalpels and classical paraffin-microtome sectioning at 5 µm. Brain specimens were prepared for 200 µm vibratome sections by embedding in 4% agarose. Sections were conserved in PBS containing 0.01% sodium azide until staining and visualization. All specimens were stained with DAPI for nuclei as background architecture. To visualize vessels we used two staining techniques. For an in vivo vessel staining we injected 50 µg isolectin-488 I.V. 2 h before sacrifice (121411, Life Technologies). For staining blood vessels on vibratome sections, we blocked with TNT containing blocking reagent (FP1012, Perkin Elmer) and permeabilized with Triton-X 100, and overnight incubated with rabbit anti-GLUT-1 primary antibody (1/100, 07-1401, Merck Millipore). After extensive washing with TNT, donkey anti-rabbit IgG—alexa fluor 555 was added overnight (1/200, A31572, Life Technologies), and sections were mounted (Dako mounting medium). Visualization of the slides was performed with confocal microscopy (SP8, Leica). Images were processed via ImageJ software.

Tumour Inoculation and Intranasal Administration.

The mice were intracranially injected with GL261-WT or GL261-BFP tumour cells as previously described [Vllasaliu, D. (2010) Int. J. Pharm. 400, 183-193]. Briefly, $0.5 \times 10^6$ tumour cells were injected at 2 mm lateral and 2 mm posterior from the bregma at a depth of 3 mm below the dura mater by using a stereotactic frame (Kopf Instruments, Tujunga, Calif.). Stereotactic inoculation was performed under sterile conditions. Intracranial tumours will develop within 3 weeks, and mice were monitored three times a week for weight and neurological deficit scale scoring. Intranasal administration was performed under 2.5% isoflurane anaesthesia. One dose for one animal for one day consisted of 24 µl of maximal concentrated chitosan nanoparticles as described before, given as 8 drops of 3 µl with 3 minutes time interval. All animal experiments were performed with permission of the Ethical Committee of the KU Leuven on laboratory animal welfare.

Immunofluorescence Analysis.

For a first set of distribution experiments, we injected isolectin conjugated with AlexaFluor 488 (I21411, Life Technologies) 2 h prior to animal sacrifice, which results in staining of blood vessels, and more specifically the tumour associated blood vessels. Dye-547 labelled anti-Gal-1 siRNA was intranasal administered 4 or 8 h prior to sacrifice. Mice were sacrificed via lethal Nembutal injection and perfused with PBS (Lonza, Belgium) followed by 4% paraformaldehyde via cardial perfusion at day 14 post tumour inoculation. Brains were prelevated, and fixated for an additional overnight incubation with 4% paraformaldehyde. Brains were extensively washed and fixed in a 4% agar solution. Subsequently, 200 µm vibratome sections were prepared and a nuclear staining was performed with DAPI (Sigma, Belgium) for 20'. Sections were mounted and closed with fluorescent mounting medium (Dako, Belgium).

In parallel, we also performed a distribution experiment to distinguish if the formulation could enter GL261 tumour cells. In these experiments, $0.5 \times 10^6$ BFP positive tumour cells were inoculated and tumour progression was allowed for 14 days. Fluorescein-loaded anti Gal-1 siRNA nanoparticles were administered for 3 consecutive days with one dose, and sacrificed 4 h after the last administration, followed by the same processing as described above. Staining of blood vessel architecture was blocked in TNB buffer (0.1M Tris pH 7.4; NaCl 150 mM; 0.5% blocking reagent Perkin Elmer, Boston) for 2 h at RT. Tissues were incubated with a rabbit anti-mouse-GLUT-1 (Millipore) diluted in TNB overnight at 4° C., washed in TNT (0.1M Tris pH 7.4; NaCl, 150 mM; 0.2% Triton X-100) and incubated with an anti-rabbit secondary antibody AlexaFluor-647 (Life Technologies) diluted in TNB overnight at 4° C.

Gal-1 Knockdown Evaluation.

Mice received 4 intranasal administered anti-Gal-1 siRNA loaded nanoparticles at day 5, 8, 12 and 15 after tumour inoculation. At day 20, or earlier if mice developed clinical signs of massive tumour burden, mice were sacrificed and perfused with PBS. For untreated mice, this was often before day 20, while for anti-Gal-1 siRNA treated mice this was at day 20. Brains were prelevated and homogenized in 2 ml tissue protein extraction buffer (78510, Thermo Scientific). Debris was removed, and supernatant was used for colourimetric protein analysis (BCA kit, Pierce, Life Technologies) and western blot analysis. For Gal-1, we used rabbit anti-Gal-1 (1/1000; Peprotech) and for Gal-3 rabbit anti-Gal-3 (1/1000; Abcam). As a protein-loading control, all blots were stained with rabbit anti-β-Actin (1/5000; Abcam). Secondary peroxidase-conjugated anti-rabbit IgG goat (1/5000; Dako) was used and visualization was performed via chemi-luminescence (western lightening, Perkin Elmer). Quantification was performed with ImageJ software. For mRNA analysis, a small piece of tumour was harvested (<30 mg), and homogenized. Subsequently, RNA was isolated and prepared for RT-qPCR as described previously. In parallel, we also evaluated the knockdown of Gal-1 via immunofluorescence staining. In brief, 200 µm vibratom sections were stained for Gal-1 (AF1163, R&D) via the staining protocol as described above for Glut1. Quantification of fluorescence intensity was measured via ImageJ, and 1 representative of each group is depicted. (FIG. 10)

Survival Analysis.

Thirty mice were inoculated with GL261-WT cells and were randomly divided in 2 groups. One group was left untreated, but also underwent isoflurane anaesthesia, and the second group received 4 doses chitosan nanoparticles loaded with anti-Gal-1 siRNA at day 5, 8, 12 and 15 after tumour inoculation. Long term survival is defined as 3 times the median survival of control mice.

Statistics.

All data were analysed with Graphpad Prism 5.0 (San Diego, Calif.). To compare two groups, a student's t test was performed. In case of comparison to anti-Gal-1 siRNA, one-tailed analysis was performed. Survival analysis was compared with Log-Rank test.

Example 1 Particle Characterization

For selection of the optimal formulation, a thorough assessment process was prepared for several parameters of paramount importance. A first selection criterion was the size of the nanoparticles. Therefore, we assessed the influence of the molecular weight of the chitosan polymer, the concentration of chitosan, and the stirring speed on the hydrodynamic size (Z-average) of the nanoparticles (Table 2). Lower molecular weight, higher stirring speed, and lower concentration of chitosan resulted in the smallest particles with an average size of 147 nm and poly-dispersity index of 0.27 (Table 3). Further dilution of chitosan (<0.7 mg/ml) did not result in formation of particles (data not shown). Zeta-potential was not influenced by these parameters and was determined to be +32 mV. For further work, the smallest nanoparticles were selected; manufactured with 50 kDa chitosan, stirred at 1300 RPM, and dissolved at 0.7 mg/ml. After production, the particles were collected by ultracentrifugation, and freeze dried without modification of size and zeta potential of the particles (Table 2). Moreover, conservation of these particles showed stability at 4° C. in a desiccator for at least 8 weeks (data not shown).

Molecular weight of the chitosan chain, stirring speed of the particle preparation and concentration of chitosan had a significant effect on the size of the prepared nanoparticles. Nanoparticles were indifferent after freeze-drying with sucrose.

TABLE 2

Critical parameters that affect the ionic gelation of nanoparticles.

| variable | | Size (nm ± SD) | Effect (p-value) |
|---|---|---|---|
| Molecular weight | 50 kDa | 162.7 ± 6.7 | Yes, p = 0.01* |
| | 90 kDa | 181.5 ± 10.1 | |
| Stirring speed | 700 RPM | 177.8 ± 2.5 | Yes, p = 0.009* |
| | 1300 RPM | 137 ± 4.6 | |
| Concentration of chitosan | 0.7 mg/ml | 128.8 ± 5.3 | Yes, p = 0.0027* |
| | 2 mg/ml | 306.1 ± 10.6 | |
| Freeze drying process | Before | 138.9 ± 3.6 | No, p = 1* |
| | After | 140.6 ± 5.4 | |

*Mann-Whitney test # Linear regression analysis.

TABLE 3

Particle characteristics.

| Particle size (nm) | Zeta potential (mV) | siRNA loading formulated (µg/ml) | siRNA loading (%) | siRNA loading after SDS (%) |
|---|---|---|---|---|
| 140.6 ± 5.4 | +32 mV | 24 | 81 ± 2.6 | 4.1 ± 2.4 |

This table describes the final nanoparticle preparation as measured by zeta sizer and SYBR green analysis. Nanoparticles encapsulate siRNA to a high amount, with an instant release in contact with detergent Conclusion: The work shown in this example confirms the feasibility to make chitosan nanoparticles by ionic gelation that can encapsulate siRNA molecules. Particles are prepared under mild conditions, which prevent degradation of the siRNA during particle preparation. More in detail, we described how particles behave when changing critical parameters as polymer length, stirring speed and dissolution of chitosan (Table 2). Consequently we described an optimized protocol to concentrate the nanoparticles to a high degree. Concentration of the nanoparticles is of paramount importance for exploitation of the nose-to-brain transport. We tested different concentrations of different lyoprotectants, and based on solubility and protection for the nanoparticles, we selected sucrose as most optimal lyoprotectant.

To further assess the relevance of the molecular weight of the chitosan molecules used for preparing the anti-Gal-1 loaded nanoparticles the efficacy of transfecting cultured GL261 cells was investigated for 20 nM siRNA containing chitosan nanoparticles, either prepared with 20 kDa or 50 kDa polymer. At day 4 and day 7 after transfecting the GL261 cells with the respective anti-Gall siRNA chitosan nanoparticles the cells were harvested and lysed. Subsequently, the Gal-1 expression in the cells was assessed by western blot analysis of the respective cell lysates. As shown in FIG. 1, at day 4 only the chitosan nanoparticles prepared with 50 kDa chitosan provided a suppression of Gal-1 expression in GL261 cells, while at day 7 the Gal-1 expression was suppressed to a similar degree in the cells treated with the 50 kDa and 20 kDa chitosan nanoparticles, respectively. Overall, the more immediate effect of the 50 kDa nanoparticles on Gal-1 expression suggests that the use 50 kDa chitosan allows for producing anti-Gal-1 siRNA loaded nanoparticles with a higher transfection efficiency than through the use of 20 kDa chitosan. These experiments further confirmed the particular selection of 50 kDa chitosan for preparing the anti-Gal-1 siRNA loaded nanoparticles for use in the in vivo study of the intranasal administration of such nanoparticles for the treatment of glioblastoma (see following examples).

Example 2 siRNA Encapsulation and Protection from Degradation

The siRNA carrier capacity of chitosan nanoparticles was evaluated by using SYBR green assay. To avoid loss of siRNA, a maximal loading capacity of 24 µg/ml siRNA was chosen for further studies: we observed that in that condition, 81% of siRNA was encapsulated into the nanoparticles. The formulated siRNA was instantaneously released upon incubation with 0,1% SDS, as indicated by a sudden loss of encapsulation efficiency (Table 3). Moreover, we also confirmed the high encapsulation efficiency via the ultracentrifugation concentration process. After three centrifugal cycles, we measured that 85% of the fluorescent siRNA is inside the pellet (data not shown).

Furthermore, the siRNA protection from degradation was evaluated with a degradation assay (FIG. 2). No degradation of siRNA was observed when the siRNA-loaded nanoparticles were incubated with RNases at 37° C. for several time periods. For better visualization, particles were immediately destroyed by adding SDS just before loading them on the gel. In contrast, free siRNA was rapidly degraded and could not be observed. These results confirm that a very high percentage of the siRNA is encapsulated into the particles, and that these particles provide an excellent protection from degradation.

Conclusion: siRNA that was incorporated into the chitosan nanoparticles was firmly complexed and showed no degradation after incubation with RNases.

Example 3 Nanoparticles Behaviour on Tumoural Cells

Attachment of the formulation was tested on both a murine GBM cell line, GL261, as well as on human primary GBM cultures. In both cases, 2 h after co-incubation in serum free media, a rapid attachment on the tumoural cells was observed (FIG. 3 A+D). To evaluate if the attachment of the particles on the GL261 tumour cells also induced a suppression of Gal-1, mRNA and protein analysis was performed (FIG. 3 B+C). For the GL261 cells, a strong and specific Gal-1 mRNA degradation was observed rapidly after transfection. After 1 week, the Gal-1 mRNA was recuperated. On protein level, a strong decrease was observed starting from day 4 after transfection until at least day 7. In parallel, the Gal-1 degradation of primary cultures was analysed (FIG. 3 E+F). In six independent primary GBM cultures, a strong decrease was notable from day 4 to day 7 post transfection.

To further investigate the biological significance of Gal-1 suppression, an assessment of the cell motility was performed via a scratch wound assay. 48 h after introducing the scratch, this assay revealed a significant lower motility profile of the GL261 cells when Gal-1 was reduced (FIG. 4). 23 h after introducing the scratch displayed a similar pattern, although the difference was not yet significant (data not shown). Gal-1 suppressed GL261 tumour cells needed more time to repopulate the surface area caused by the scratch.

Conclusion: This example shows that a rapid attachment to the cells when applying the chitosan particles to GBM cells (FIG. 3). To evaluate if the particles are also taken up by the GBM cells we examined Gal-1 on mRNA and protein level for the murine cell line, and on protein level for 6 individual tumour cell lines. In all cases, we observed an inhibition of Gal-1 that lasted for several days after a single administration of the particles, although GBM cells are rapidly dividing cells. As a control, we checked the specificity of the siRNA via Galectin-3 western blot, where we did not observe a decrease of Gal-3. The mechanism of the siRNA release from the chitosan polymer is most likely to rely on the proton sponge effect creating lysosomal damage by scavenging of $H^+$ by the primary amines of the chitosan polymer [Nel, A. E. et al. (2009) Nature materials 8, 543-557]. Furthermore, we were able to confirm the effect on migration of GBM cells when Gal-1 was reduced (FIG. 4) [Camby I. et al. (2002) J. Neuropathol. Exp. Neurol. 61, 585-596].

Example 4 Formulation-Mediated Epithelial Modulation

The modulation of tight-junctions by chitosan-based formulations was evaluated with Calu-3 monolayers. First, we visualized the disperse distribution of the chitosan nanoparticles on the apical side of a Calu-3 monolayer (FIG. 5 A). At a concentration of 0.06% chitosan nanoparticles and 2 h after administration, a significant decrease in resistance over the monolayer was observed. This decrease in resistance was transient and recuperated at latest by 24 h after particles incubation (data not shown). This decrease in resistance resulted in a trend towards a higher permeability of the monolayer for small hydrophilic probes, e.g. FD4 (FIG. 5 B+C). In line with literature reports, the internalization of tight junctions was observed after chitosan administration on this monolayer (FIG. 5 D). We observed a disturbance of the intact monolayer, as monitored by staining the monolayer for ZO-1 protein.

For the purpose of intranasal administration, and reaching the CNS, it is necessary to transiently disturb the epithelial layer. Under physiological conditions, the mucosal layer is closely interconnected via tight-junctions. We observed on the calu-3 cell line monolayer a significant drop of the resistance when applying the chitosan formulation at 0.06% (FIG. 5). When removing the formulation, the resistance gently recuperated, and at most after 24 h the resistance returned to baseline. We noted also that there was a consistent drop in resistance in the medium condition, which we believe to be attributed to the change in temperature, humidity and $CO_2$, $O_2$ content necessary for performing the resistance measurement. To assess whether the drop in resistance also translates into an increased passage of molecules across the barrier, we incubated the monolayer with nanoparticles and FD4. We observed a trend towards higher passages of FD4. Interestingly, however the 0.03% concentration did not result in a drop in resistance. We have tried to assess the passage of fluorescent siRNA incorporated into the chitosan nanoparticles. We observed that the chitosan particles showed high affinity for polyester, and although particles were smaller than the insert pore size (0.4 μm), very low passage could be observed (data not shown), even without seeding cells onto the insert. We examined if we could detect the opening tight junctions via immunofluorescence staining. We observed a disappearance of the ZO-1 molecule when applying chitosan particles after 2 h both in the 0.03% and 0.06% condition, which might explain the increased passage in FD4. These results suggest the internalization of tight junctions upon chitosan stimulus.

Example 5 Transport to the Central Nervous System

At first entrance barrier, the nasal mucosa was assessed by confocal microscopy observation of the appearance of red dye-547 labelled siRNA in preparations of the nasal mucosa of a control untreated mouse and of mice sacrificed 4 h and 8 h, respectively, after the intranasal administration of chitosan nanoparticles comprising dye-547 labelled siRNA. In control untreated mice, no red signal could be observed. In treated mice, we could observe red nanoparticles in the nasal mucosa 4 h and 8 h after administration. To further delineate into detail the passage through the epithelial layer, we intranasally administered chitosan nanoparticles loaded with red dye-547 labelled siRNA to mice for 3 consecutive days and sacrificed those 4 h after the last administration for processing to classical paraffin sections. A strong presence of dye-547 labelled siRNA was detected on the nasal mucosa. Especially on the mucus layer a strong concentration is present, but also transport over the columnar epithelium is visible, into the lamina propria. Transport across the nasal mucosa seems very likely to be the primary requisite to reach the central nervous system. To further assess the transport towards the CNS, the olfactory bulbus and the hindbrain, which are well described entry points towards the central nervous system, were assessed for the presence of siRNA. The role of the olfactory bulbus in said transport was assessed using confocal microscopy observation of the appearance of red dye-547 labelled siRNA in preparations of the olfactory bulbus of a control untreated mouse and of mice sacrificed 4 h and 8 h, respectively, after the intranasal administration of chitosan nanoparticles comprising dye-547 labelled siRNA. A thorough assessment of the olfactory bulbus indicates no presence of fluorescence in control untreated mice. However in treated mice, we observe a fluorescent signal at the tip of the olfactory bulbus 4 h after administration. We observe a more diffuse distribution of the dye-547 labelled siRNA at 8 h administration. In order to assess the long term effect on the entry at the olfactory bulbus, we also monitored mice that received three administrations over three days, and which were sacrificed 4 h after the last administration. Here we observe an intense distribution in the glomerular layer of the olfactory bulbus, and a more diffuse distribution into the external plexiform layer. Furthermore, we also assessed the transport to the olfactory bulbus and hindbrain via a similar confocal microscopy technique which involved the amplification of the fluorescein-labelled siRNA with an anti FITC-FITC conjugated antibody. When using this technique fluorescein-siRNA could be observed in the olfactory bulbus at both 4 and 24 hours after administration to the mice of fluorescein-siRNA loaded nanoparticles. However, the presence of siRNA was not only at the side of the olfactory bulbus, but also in the hindbrain at both 4 and 24 hours after administration to the mice of fluorescein-siRNA loaded nanoparticles. Both loci are suggestive for the aforementioned pathways. Trigeminal nerves were also examined, but no clear presence of fluorescent siRNA could be observed (data not shown).

Within the in vivo assessment, we validated the transport across the nasal mucosa. We observed a rapid spread of the formulation already after 4 h in the nasal mucosa, while in control, untreated mice no fluorophore was to be observed. To distinguish the mode of transport is difficult; however some pictures suggest a transport along the vessels, confirming the perivascular transport into the CNS. The dense accumulation around the vasculature might also be a source of rapid systemic distribution. Also after 8 h, we still observe the fluorescence present on the nasal mucosa. To observe the long term effects on the mucosa, we performed a distribution experiment where we intranasally administered chitosan nanoparticles loaded with dye-547 labelled siRNA for 3 consecutive days before sacrificing the mouse 4 hours after the last administration. These sections were processed by paraffin embedding, revealing a high signal in the lamina propria. Also the mucus layer coloured positive for the dye-547 labelled siRNA, and passage through the columnar epithelium cells could also be observed. In preliminary distribution experiments, we did observe an increase of fluorophore tagged siRNA in the plasma and liver after 6 h (data not shown). To evaluate the distribution into the CNS we first focused on the olfactory bulbus, as this is the main entry route. Via DAPI nuclei staining, we could make a clear distinction of the glomerular layer, characterized by profound round-shaped organizations, if the bulbus was dissected to its full extent. We observed a strong and increasing signal of the dye-547 siRNA 4 h and 8 h after a single administration. Furthermore, after 3 daily administrations this signal was more abundant over the entire region of the olfactory bulbus. These observations clearly underline the importance and feasibility of the direct transport of the nasal cavity to the central nervous system via the olfactory pathway. Next, we also were interested to find the presence of siRNA in the hindbrain, as an alternative pathway to the CNS via the trigeminal nerves. To further amplify our signal, we stained the fluorescein-labelled siRNA with an FITC coupled anti-fluorescein antibody. In these experiments, the vessels were not detected via isolectin-staining, but via the GLUT-1 staining. We confirmed in these experiments the presence in the olfactory region, but we also found a clear signal of the siRNA in the hindbrain, 4 h and 24 h after a single administration. Colour pictures illustrating the above mentioned observations are available in Van Woensel et al., (2016) *J. Contr. Rel.* 227, 71-81.

Example 6 Distribution in the Tumour Micro-Environment

As we demonstrated earlier, the anti-Gal-1 siRNA formulation with chitosan nanoparticles can efficiently reach the central nervous system. To address the question whether we can reach a central nervous system tumour, we inoculated mice with GL261-WT cells, and allowed tumours to grow for 14 days, until a solid mass was present. Using confocal microscopy observation of the appearance of red dye-547 labelled siRNA in the tumour environment of a control untreated mouse and of mice sacrificed 4 h and 8 h, respectively, after the intranasal administration of chitosan nanoparticles comprising dye-547 labelled siRNA. Via the isolectin staining for tumour-associated blood vessels, we could clearly define the tumour area on the section. Vessels were clearly dilated and seemed to lack an organized structure, suggestive for impaired blood flow and oxygen supply. In untreated control mice, no siRNA-associated fluorophore could be detected. In the experimental group, we injected mice intranasally with dye-547 loaded anti-Gal-1 siRNA, corresponding to the red colour. After a single administration, we already noticed an abundant signal in the tumour micro environment. After 4 h this signal seemed more particulated, and after 8 h more diffuse. This observation clearly demonstrated the feasibility of reaching the tumour micro-environment via the intranasal route. Question remained if the anti-Gal-1 siRNA could reach also the tumour cells, which are besides blood vessels and macrophages, the major cell populations that produce Gal-1 in the glioma. Therefore, we injected GL261-BFP positive tumour cells that can be detected under confocal microscopy (FIG. 6). Both in the tumour centre (FIG. 6A) as in the tumour border (FIG. 6B), we could find anti-Gal-1 fluorescein-siRNA signal 4 h after the intranasal administration of fluorescein-siRNA loaded nanoparticles. Moreover, we could observe also a strong signal associated with the blood vessels, despite perfusion, suggestive for presence in the endothelial cells.

Overall these results clearly show that the anti-Gall siRNA reaches the tumour cells following intranasal administration using the chitosan nanoparticulate delivery form. Colour pictures illustrating the above mentioned observations are available in Van Woensel et al. (2016) J. *Control. release* 227, 71-81.

Example 7 Intratumoural Reduction of Gal-1

Above, we observed the presence of the anti-Gal-1 siRNA in the tumour micro-environment. To further investigate the functionality of the RNA interference molecules, we needed to determine the amount of Gal-1. In previous in vitro results, we observed a strong decrease of Gal-1, 4 to 7 days post transfection. This biological Gal-1 turnover was also observed after intra-tumoural injection (data not shown) of the anti-Gal-1 siRNA. Therefore, we administered the anti-Gal-1 siRNA loaded nanoparticles until day 15 post tumour inoculation, and then sacrificed the mice at day 20 post tumour inoculation. In two independent experiments, we observed a strong decrease of Gal-1 in the treated mice, as compared to control, untreated mice. Moreover, we also noticed that not only Gal-1 was reduced, but also Galectin-3 (Gal-3) which also displays tumour promoting properties. The decrease in Gal-1 was more substantial than the decrease in Gal-3, but not significant (p=0.09). We also performed RT-qPCR on a small piece of the tumour (<30 mg) at day 20 post tumour inoculation. This revealed a small, but not significant decrease in Gal-1 in the treated animals. Based on our previous in vitro findings, it was expected that mRNA is less reduced 5 days post administration than protein levels. (FIGS. 7 and 8)

We observed a strong significant decrease of Gal-1 in treated mice, suggesting a specific knockdown. Surprisingly and in contrast to the in vitro findings (see Example 3), in vivo we did find a significant decrease for Gal-3. This suggests a biological interplay between Gal-1 and Gal-3.

Moreover, we confirmed the decrease of Gal-1 via immunofluorescence staining (FIG. 10).

Example 8 Increased Survival of Treated Mice

Mice were inoculated with GL261-WT and randomly divided into two groups. We observed a prolonged survival of mice treated with intranasal anti-Gal-1 siRNA formulation. The median survival shifted from 19 days in controls to 23 days in treated mice. Early in the disease progression, there was only a small survival benefit to be observed, but later the differences in the curves becomes larger. We also observed long term survivors in the treated group of mice while in contrast all the untreated mice died (FIG. 9). Furthermore, we noted that empty particles (containing no siRNA) had no effect on survival of tumour bearing mice, underlining the importance of Gal-1 in halting or slowing tumour progression.

The invention claimed is:

1. Chitosan nanoparticles comprising:
   crosslinked chitosan; and
   small interfering RNA (siRNA),
   wherein the siRNA is encapsulated within the chitosan nanoparticles,
   wherein chitosan molecules in said chitosan nanoparticles have a Mr of between 30 and 60 kDa, and
   wherein the hydrodynamic diameter (z-average) of said chitosan nanoparticles is between 100 and 200 nm.

2. The chitosan nanoparticles according to claim 1, wherein the chitosan molecules in said chitosan nanoparticles have a Mr of between 45 and 55 kDa.

3. The chitosan nanoparticles according to claim 1, wherein the poly-dispersity index of said chitosan nanoparticles is between 0.15 and 0.40.

4. A pharmaceutical composition, comprising the chitosan nanoparticles of claim 1 combined with excipients suitable for administration via intranasal delivery.

5. A method for the preparation of the chitosan nanoparticles as defined in claim 1, said method comprising the steps of:
   1) dissolving chitosan polymers having a molecular weight between 30 and 60 kDa in an acetic solution;
   2) dissolving the siRNA in a solution of a negatively charged compound suitable for crosslinking chitosan polymers;
   3) adding the solution comprising the siRNA and said negatively charged compound to the acetic solution of the dissolved chitosan polymers of step 1) while stirring or mixing said combined solutions in order to obtain a formation of suspended chitosan nanoparticles comprising the siRNA;
   4) collecting said chitosan nanoparticles using filtration, centrifugation or other suitable technique for isolating the suspended chitosan nanoparticles.

6. The method according to claim 5, wherein said chitosan polymers have a molecular weight between 45 and 55 kDa.

7. The method according to claim 5, wherein between 30 and 60 µg of the siRNA is added per mg of the chitosan polymers.

8. The chitosan nanoparticles according to claim 1, comprising between 30 and 60 µg of the siRNA per mg of the crosslinked chitosan.

9. The chitosan nanoparticles according to claim 1, wherein at least part of the chitosan molecules carry one or more poly-ethylene glycol units.

10. The method according to claim 5, wherein the chitosan polymers are cross-linked via sodium tripolyphosphate.

11. The method according to claim 10, wherein a chitosan to sodium tripolyphosphate weight ratio is between 2.5 and 3.0.

12. The chitosan nanoparticles according to claim 1, further comprising a lyoprotectant.

13. The chitosan nanoparticles according to claim 12, wherein said lyoprotectant is sucrose or trehalose.

14. The chitosan nanoparticles according to claim 12, wherein said lyoprotectant is sucrose and wherein the chitosan nanoparticle to sucrose ratio typically varies between 1/2 to 1/16.

15. The chitosan nanoparticles according to claim 12, wherein said lyoprotectant is trehalose and wherein the chitosan nanoparticle to sucrose ratio typically varies between 1/8 to 1/28.

* * * * *